United States Patent [19]

Kleinman

[11] Patent Number: 5,686,434
[45] Date of Patent: Nov. 11, 1997

[54] 3-ARYL-2-ISOXAZOLINES AS ANTIINFLAMMATORY AGENTS

[75] Inventor: Edward Fox Kleinman, Stonington, Conn.

[73] Assignee: Pfizer Inc., New York, N.Y.

[21] Appl. No.: 640,945

[22] PCT Filed: Oct. 12, 1994

[86] PCT No.: PCT/IB94/00313

§ 371 Date: May 15, 1996

§ 102(e) Date: May 15, 1996

[87] PCT Pub. No.: WO95/14680

PCT Pub. Date: Jun. 1, 1995

Related U.S. Application Data

[63] Continuation of Ser. No. 157,241, Nov. 26, 1993, abandoned.

[51] Int. Cl.$^6$ .................. C07D 261/04; C07D 261/10; C07D 261/12; A61K 31/42
[52] U.S. Cl. .................. 514/92; 514/378; 514/379; 514/380; 548/111; 548/113; 548/119; 548/240; 548/242; 548/243; 548/244; 548/245
[58] Field of Search .................. 548/240, 242, 548/243, 244, 245, 111, 119, 113; 514/379, 378, 380, 92

[56] References Cited

U.S. PATENT DOCUMENTS

| | | | |
|---|---|---|---|
| 4,889,551 | 12/1989 | Oda et al. | 71/88 |
| 4,912,120 | 3/1990 | Castelhano et al. | 514/380 |
| 4,924,002 | 5/1990 | Kostlan | 548/206 |
| 4,933,464 | 6/1990 | Markofsky | 548/247 |
| 4,952,700 | 8/1990 | Markofsky et al. | 548/240 |
| 5,006,515 | 4/1991 | Schwab et al. | 514/89 |
| 5,208,251 | 5/1993 | Belliotti et al. | 514/372 |
| 5,273,989 | 12/1993 | Schwab et al. | 548/240 |

FOREIGN PATENT DOCUMENTS

| | | |
|---|---|---|
| 0247725 | 12/1987 | European Pat. Off. . |
| 0401903 | 12/1990 | European Pat. Off. . |
| 8706576 | 11/1987 | WIPO . |
| 9107178 | 5/1991 | WIPO . |
| 9115451 | 10/1991 | WIPO . |
| 9203053 | 3/1992 | WIPO . |
| 9207567 | 5/1992 | WIPO . |
| 9219594 | 11/1992 | WIPO . |
| 9307141 | 4/1993 | WIPO . |

OTHER PUBLICATIONS

J. A. Beavo et al., TiPS, Apr. 1990, vol. 11, pp. 150–155.
C. D. Nicholson et al., TiPS, Jan. 1991, vol. 12, pp. 19–27.
E. W. Sutherland et al., Pharmacol. Rev., 1960, 12, pp. 265–299.
M. W. Verghese et al., J. Mol. Cell Cardiol., 1989, 12 (Suppl. II), S61.
Tetrahedron, vol. 37, No. 19, pp. 3365–3376, Kumagi et al., 1981.
J. Am. Chem. Soc., 107, pp. 5310–5312, Nishiyama et al., 1985.
J. Heterocyclic Chem., 27, pp. 275–278, Jarrar et al., 1990.
CA 96:84853y, Kumagai et al., p. 527, 1982.
CA 103: 160616d, Nishiyama et al., p. 123, 1985.
CA 113: 58998z, Jarrar et al., p. 687, 1990.
0039867: Japan, Derwent Publication Abstract, No. 88-088442/13, Feb. 1988.

*Primary Examiner*—Mukund J. Shah
*Assistant Examiner*—Deepak R. Rao
*Attorney, Agent, or Firm*—Peter C. Richardson; Gregg C. Benson; A. Dean Olson

[57] ABSTRACT

This invention relates to 3-aryl-2-isoxazoline compounds which are selective inhibitors of phosphodiesterase type IV ($PDE_{IV}$). The 3-aryl-2-isoxazolines are useful in the treatment of AIDS, asthma, arthritis, bronchitis, chronic obstructive pulmonary disease, psoriasis, allergic rhinitis, dermatitis, shock, atopic dermatitis, rheumatoid arthritis and osteoarthritis. This invention also relates to pharmaceutical compositions useful therefor.

16 Claims, No Drawings

3-ARYL-2-ISOXAZOLINES AS ANTIINFLAMMATORY AGENTS

CROSS REFERENCE TO RELATED APPLICATIONS

This application is the national stage of PCT Application No. PCT/IB94/00313 having an international filing date of Oct. 12, 1994, which is a continuation of U.S. application Ser. No. 08/157,241, filed Nov. 26, 1993, now abandoned.

BACKGROUND OF THE INVENTION

This invention relates to a series of 3-aryl-2-isoxazoline compounds which are selective inhibitors of phosphodiesterase (PDE) type IV and as such are useful in the treatment of AIDS, asthma, arthritis, bronchitis, chronic obstructive airways disease, psoriasis, allergic rhinitis, dermatitis and other inflammatory diseases.

This invention also relates to the pharmaceutically acceptable salts of said compounds; to a method of using such compounds in inhibiting $PDE_{IV}$, the treatment of inflammatory conditions and the treatment of AIDS, asthma, arthritis, bronchitis, chronic obstructive airways disease, psoriasis, allergic rhinitis and dermatitis in mammals, especially humans; and to pharmaceutical compositions useful therefor.

The "inflammatory conditions" which can be treated according to this invention include, but are not limited to, chronic obstructive pulmonary disease, septic shock, atopic dermatitis, bronchitis, rheumatoid arthritis and osteoarthritis.

Since the recognition that cyclic AMP is an intracellular second messenger (E. W. Sutherland, and T. W. Rall, *Pharmacol. Rev.*, 1960, 12, 265), inhibition of the phosphodiesterases has been a target for modulation and, accordingly, therapeutic intervention in a range of disease processes. More recently, distinct classes of PDE have been recognized (J. A. Beavo and D. H. Reifsnyder, *TiPS*, 1990, 11, 150), and their selective inhibition has led to improved drug therapy (C. D. Nicholson, R. A. Challiss and M. Shahid, *TiPS*, 1991, 12, 19). More particularly, it has been recognized that inhibition of $PDE_{IV}$ can lead to inhibition of inflammatory mediator release (M. W. Verghese et al., *J. Mol. Cell Cardiol.*, 1989, 12 (Suppl. II), S 61) and airway smooth muscle relaxation (T. J. Torphy in *Directions for New Anti-Asthma Drugs*, eds S. R. O'Donnell and C. G. A. Persson, 1988, 37, Birkhauser-Verlag). Thus, compounds that inhibit $PDE_{IV}$, but which have poor activity against other PDE types, would inhibit the release of inflammatory mediators and relax airway smooth muscle without causing cardiovascular effects or antiplatelet effects.

Certain isoxazoline phosphonic acid compounds are disclosed to be useful for the treatment of diseases of the immune system in U.S. Pat. No. 5,006,515.

Certain catechol diethers are disclosed to be useful as $PDE_{IV}$ inhibitors and as such are useful in the treatment of inflammatory diseases, AIDS, asthma, arthritis, bronchitis, chronic obstructive airways disease, psoriasis, allergic rhinitis and dermatitis, in copending U.S. patent application, Ser. No. 07/984,408 filed Dec. 2, 1992, which application is assigned to the assignee hereof.

Certain pyrimidone compounds have been disclosed to be useful as antidepressants by Saccomano et al., in European Patent Application EPO 247 725 A2. The same pyrimidone compounds have been disclosed to be useful against asthma and certain skin disorders in International Patent Application No. PCT/US90/02162, published May 30, 1991 as International Publication Number WO 91/07178.

SUMMARY OF THE INVENTION

This invention is concerned with a series of 3-aryl-2-isoxazoline compounds and to the pharmaceutically acceptable salts of such compounds. These new compounds are selective inhibitors of $PDE_{IV}$, and as such are useful in the treatment of inflammatory conditions, AIDS, asthma, arthritis, bronchitis, chronic obstructive airways disease, psoriasis, allergic rhinitis and dermatitis in mammals, especially humans.

The compounds of the present invention are of the formula (I)

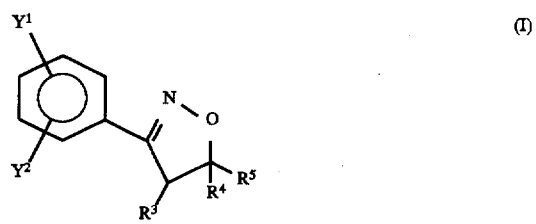

the racemic, racemic-diastereomeric mixtures and optical isomers of said compounds and the pharmaceutically acceptable salts thereof wherein $Y^1$ and $Y^2$ are independently selected from the group consisting of hydrogen, $(C_1-C_6)$alkyl, optionally substituted phenylalkyl having 1 to 6 carbons in the alkyl portion, optionally substituted phenoxyalkyl having 1 to 6 carbons in the alkyl portion, $(C_3-C_7)$cycloalkyl, fluoro, chloro, bromo, iodo, $-OR^1$ and $-OR^2$;

wherein the aromatic portion of the optionally substituted phenylalkyl, and the aromatic portion of the optionally substituted phenoxyalkyl are optionally independently substituted with $(C_1-C_4)$alkyl, $(C_1-C_4)$alkoxy, halogen or $CF_3$;

$R^1$ is alkyl having 1 to 3 carbons, fluoromethyl, difluoromethyl or trifluoromethyl;

$R^2$ is $(C_1-C_3)$alkyl, $(C_3-C_7)$cycloalkyl, alkoxyalkyl having 3 to 7 carbons in the alkoxy portion and 2 to 4 carbons in the alkyl portion, optionally substituted phenoxyalkyl having 2 to 6 carbons in the alkyl portion, optionally substituted phenylalkyl having 1 to 6 carbons in the alkyl portion, bicycloalkyl having 6 to 9 carbons or optionally substituted indanyl;

wherein the aromatic portion of the optionally substituted phenylalkyl, the aromatic portion of the optionally substituted phenoxyalkyl and the optionally substituted indanyl are optionally independently substituted with $(C_1-C_4)$alkyl, $(C_1-C_4)$alkoxy, halogen or $CF_3$;

$R^3$ is hydrogen, $(C_1-C_3)$alkyl, mono-hydroxyalkyl having 1 to 3 carbons or alkoxyalkyl having 1 to 3 carbons in the alkyl portion and 1 to 3 carbons in the alkoxy portion;

$R^4$ is hydrogen, $(C_1-C_5)$alkyl, $-COOH$, alkoxyalkyl having 1 to 3 carbons in the alkyl portion and 1 to 3 carbons in the alkoxy portion, N-alkylaminoalkyl having 1 to 3 carbons in the alkylamino portion and 1 to 3 carbons in the alkyl portion or N,N-dialkylaminoalkyl having a total of 2 to 6 carbons in the dialkylamino portion and 1 to 3 carbons in the alkyl portion;

or $R^3$ and $R^4$ are taken together with the carbon atoms to which they are attached and form $-CH_2OCH_2OCH_2-$; and $R^5$ is hydrogen, $-CHO$, amino, aminoalkyl having 1 to 3 carbons,

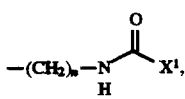

mono-hydroxyalkyl having 1 to 3 carbons, —(CH$_2$)$_b$—COOR$^6$, —COR$^7$, —(CH$_2$)$_m$CO$_2$H, (C$_1$–C$_4$)alkyl, hydroxy, —(CH$_2$)$_q$CONX$^2$X$^3$, —(CH$_2$)$_r$SO$_2$NX$^4$X$^5$, —(CH$_2$)$_t$PO$_3$H$_2$ or

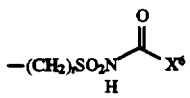

wherein b is 0 or an integer from 1 to 6;
m, n, q, r, s and t are independently 0, 1, 2, 3 or 4;
R$^6$ and R$^7$ are each independently (C$_1$–C$_4$)alkyl;
X$^1$ is hydrogen, (C$_1$–C$_4$)alkyl, —O(C$_1$–C$_4$)alkyl or alkoxyphenyl having one to four carbon atoms in the alkoxy portion;
X$^2$, X$^3$, X$^4$ and X$^5$ are each independently hydrogen or (C$_1$–C$_3$)alkyl; and
X$^6$ is (C$_1$–C$_3$)alkyl or phenyl;
provided that when R$^1$ is (C$_1$–C$_3$)alkyl, R$^2$ is (C$_1$–C$_3$)alkyl, R$^3$ is hydrogen, and R$^4$ is hydrogen then R$^5$ is not —(CH$_2$)$_t$PO$_3$H$_2$; and
when R$^4$ is —COOH then R$^5$ is not —COOH; and that both Y$^1$ and Y$^2$ cannot be hydrogen at the same time.

A preferred group of compounds or the pharmaceutically acceptable salts thereof of this invention are those compounds of the formula (I) wherein Y$^1$ is —OR$^1$ and is attached to the 4-position of the phenyl ring and Y$^2$ is —OR$^2$ and is attached to the 3-position of the phenyl ring.

A more preferred group of compounds or the pharmaceutically acceptable salts thereof of this invention are those compounds of the formula (I) wherein Y$^1$ is —OR$^1$ and is attached to the 4-position of the phenyl ring and Y$^2$ is —OR$^2$ and is attached to the 3-position of the phenyl ring, wherein R$^1$ is methyl; R$^2$ is (C$_3$–C$_7$)cycloalkyl, bicycloalkyl having 6 to 9 carbons, or phenylalkyl having 1 to 6 carbons in the alkyl portion; R$^3$ is hydrogen or (C$_1$–C$_3$)alkyl; R$^4$ is hydrogen or (C$_1$–C$_5$)alkyl; and R$^5$ is —(CH$_2$)$_m$CO$_2$H, —CHO, —COCH$_3$, amino, hydroxy, mono-hydroxyalkyl having 1 to 3 carbons, aminoalkyl having 1 to 3 carbons, or

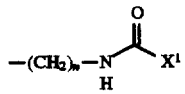

wherein X$^1$ is (C$_1$–C$_4$)alkyl or alkoxyphenyl having one to four carbon atoms in the alkoxy portion and n is 0 or an integer from 1 to 3.

Another more preferred group of compounds or the pharmaceutically acceptable salts thereof are those compounds of the formula (I) wherein Y$^1$ is —OR$^1$ and is attached to the 4-position of the phenyl ring and Y$^2$ is —OR$^2$ and is attached to the 3-position of the phenyl ring, wherein R$^1$ is methyl; R$^2$ is 5-phenylpentyl; R$^3$ is hydrogen; R$^4$ is hydrogen or CH$_3$ and R$^5$ is —(CH$_2$)$_s$PO$_3$H$_2$ wherein s is 0 or 1.

Further, another more preferred group of compounds or the pharmaceutically acceptable salts thereof are those compounds of the formula (I) wherein Y$^1$ is —OR$^1$ and is attached to the 4-position of the phenyl ring and Y$^2$ is —OR$^2$ and is attached to the 3-position of the phenyl ring, wherein R$^1$ is methyl; R$^2$ is cyclopentyl; R$^3$ is hydrogen; R$^4$ is hydrogen and R$^5$ is —(CH$_2$)$_s$PO$_3$H$_2$ wherein s is 0.

Furtherstill, another more preferred group of compounds or the pharmaceutically acceptable salts thereof are those compounds of the formula (I) wherein Y$^1$ is —OR$^1$ and is attached to the 4-position of the phenyl ring and Y$^2$ is —OR$^2$ and is attached to the 3-position of the phenyl ring, wherein R$^1$ is methyl, R$^2$ is 4-phenylbutyl, 5-phenylpentyl or cyclopentyl, R$^3$ is hydrogen or (C$_1$–C$_3$)alkyl; R$^4$ is hydrogen or (C$_1$–C$_5$)alkyl; and R$^5$ is —(CH$_2$)$_m$CO$_2$H, —CHO, —COOH$_3$, amino, hydroxy, mono-hydroxyalkyl having 1 to 3 carbons, aminoalkyl having 1 to 3 carbons, or

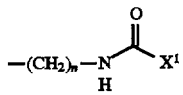

wherein X$^1$ is (C$_1$–C$_4$)alkyl or alkoxyphenyl having one to four carbon atoms in the alkoxy portion and n is 0 or an integer from 1 to 3.

Yet another more preferred group of compounds or the pharmaceutically acceptable salts thereof are those compounds of the formula (I) wherein Y$^1$ is —OR$^1$ and is attached to the 4-position of the phenyl ring and Y$^2$ is —OR$^2$ and is attached to the 3-position of the phenyl ring, wherein R$^1$ is methyl; R$^2$ is 5-phenylpentyl; R$^3$ is hydrogen or (C$_1$–C$_3$)alkyl; R$^4$ is hydrogen or (C$_1$–C$_5$)alkyl and R$^5$ is —(CH$_2$)$_m$CO$_2$H, —CHO, —COCH$_3$, amino, hydroxy, mono-hydroxyalkyl having 1 to 3 carbons, aminoalkyl having 1 to 3 carbons, or

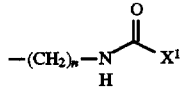

wherein X$^1$ is (C$_1$–C$_4$)alkyl or alkoxyphenyl having one to four carbon atoms in the alkoxy portion and n is 0 or an integer from 1 to 3.

Yet still another more preferred group of compounds or the pharmaceutically acceptable salts thereof are those compounds of the formula (I) wherein Y$^1$ is —OR$^1$ and is attached to the 4-position of the phenyl ring and Y$^2$ is —OR$^2$ and is attached to the 3-position of the phenyl ring, wherein R$^1$ is methyl; R$^2$ is 5-phenylpentyl; R$^3$ is hydrogen or (C$_1$–C$_3$)alkyl; R$^4$ is hydrogen or (C$_1$–C$_5$)alkyl and R$^5$ is —(CH$_2$)$_m$CO$_2$H, —CHO, —COCH$_3$, hydroxy or mono-hydroxyalkyl having 1 to 3 carbons.

A most preferred group of compounds or the pharmaceutically acceptable salts thereof are those compounds of the formula (I) wherein Y$^1$ is —OR$^1$ and is attached to the 4-position of the phenyl ring and Y$^2$ is —OR$^2$ and is attached to the 3-position of the phenyl ring, wherein R$^1$ is methyl; R$^2$ is 5-phenylpentyl; R$^3$ is hydrogen or (C$_1$–C$_3$) alkyl; R$^4$ is hydrogen or (C$_1$–C$_5$)alkyl and R$^5$ is —(CH$_2$)$_m$CO$_2$H.

Yet still another most preferred group of compounds or the pharmaceutically acceptable salts thereof are those compounds of the formula (I) wherein Y$^1$ is —OR$^1$ and is attached to the 4-position of the phenyl ring and Y$^2$ is —OR$^2$ and is attached to the 3-position of the phenyl ring, wherein R$^1$ is methyl; R$^2$ is 5-phenylpentyl; R$^3$ is hydrogen; R$^4$ is hydrogen or (C$_1$–C$_5$)alkyl and R$^5$ is —(CH$_2$)$_m$CO$_2$H wherein m=0.

A particularly preferred group of compounds or the pharmaceutically acceptable salts thereof are those compounds of the formula (I) wherein $Y^1$ is —$OR^1$ and is attached to the 4-position of the phenyl ring and $Y^2$ is —$OR^2$ and is attached to the 3-position of the phenyl ring, wherein $R^1$ is methyl; $R^2$ is 5-phenylpentyl; $R^3$ is hydrogen; $R^4$ is hydrogen, methyl, ethyl or propyl and $R^5$ is —$(CH_2)_mCO_2H$ wherein m=0.

Most particularly preferred compounds of this invention are (+) or (−)-5-ethyl-3-[4-methoxy-3-(5-phenylpentyloxy)]phenyl-2-isoxazoline-5-carboxylic acid. Of the two, (−)-5-ethyl-3-[4-methoxy-3-(5-phenylpentyloxy)]-phenyl-2-isoxazoline-5-carboxylic acid is the more preferred compound.

The term alkyl encompasses both straight and branched chains. The aromatic portion of the optionally substituted phenylalkyl, the aromatic portion of the optionally substituted phenoxyalkyl and the optionally substituted indanyl may be substituted by one or more substituents.

DETAILED DESCRIPTION OF THE INVENTION

The compounds of the present invention having the formula (I) are comprised of the racemic, racemic-diastereomeric mixtures and optical isomers of said compounds and the pharmaceutically acceptable salts thereof. The compounds of the present invention, having the formula I as defined above, are readily and generally prepared by the following reaction processes.

Compounds of the formula (I) wherein $R^5$ is a carboxylic acid can be synthesized by mixing a methanol solution of the corresponding alkyl ester, wherein $R^5$ is ethyl ester, with an aqueous solution of an inorganic base such as KOH. The mixture is stirred at room temperature until the reaction is substantially complete. The reaction mixture is worked-up according to methods well-known to those skilled in the art.

Compounds of the formula (I) wherein $R^5$ is carboxymethyl (—$CH_2CO_2H$) are synthesized by reacting a compound of the formula (I) wherein $R^5$ is hydroxymethyl (—$CH_2OH$) with p-toluenesulfonyl chloride in the presence of a tertiary amine such as triethylamine in an inert solvent at 0° C. to 50° C. to give a compound of the formula (I) wherein $R^5$ is —$CH_2OTs$, which is reacted with lithium, sodium or potassium cyanide in an inert solvent such as DMSO at 0° C. to 100° C. to give a compound of the formula (I) wherein $R^5$ is —$CH_2CN$, which is hydrolyzed with an inorganic base such as KOH in water and an alcoholic solvent at room temperature to 100° C.

The compounds of formula (I) wherein $R^5$ is an aldehyde can be synthesized by dissolving the corresponding compound of formula (I) wherein $R^5$ is —CONH-alkyl in a dry inert solvent such as tetrahydrofuran, decreasing the temperature of the solution to between −65° to −78° C. and then adding dropwise 3 to 5 equivalents of diisobutylaluminum hydride (DIBAL-H) in hexane. The reaction mixture is maintained at about −78° C. for about 30 to 60 minutes and then allowed to warm to room temperature. The reaction mixture is worked-up according to methods well known to those skilled in the art. The resulting aldehyde compound can be optionally reduced to obtain the corresponding alcohol. The aldehyde compound is dissolved in an alcoholic solvent and treated with sodium borohydride; the mixture is stirred at room temperature until the reaction is substantially complete.

Compounds of the formula (I) wherein $R^5$ is hydroxy can be synthesized by dissolving the corresponding acyloxy derivative, such as when $R^5$ is —$OCOCH_3$, in an alcoholic solvent and treating the solution with approximately 1.1 equivalents of sodium methoxide. The reaction mixture is stirred at room temperature until the reaction is substantially complete, which is usually about 1 hour.

Compounds of the formula (I) wherein $R^5$ is a monohydroxyalkyl, are synthesized by reducing the corresponding ester, wherein $R^5$ is an alkyl ester, with diisobutylaluminum hydride (DIBAL-H) according to the following procedure. A compound of formula (I) wherein $R^5$ is a methyl or ethyl ester, is dissolved in THF and chilled to about −78° C. Approximately 2 to 4 equivalents of DIBAL-H in hexane is added to the cold THF mixture. The solution is warmed to about −30° C. and then quenched with a dilute solution of HCl.

Alternatively, the compounds of formula (I) wherein $R^5$ is hydroxymethyl, are synthesized by reducing a compound of formula (I) wherein $R^5$ is an aldehyde. The aldehyde compound is dissolved in an alcoholic solvent and treated with sodium borohydride; the mixture is stirred at room temperature until the reaction is substantially complete. Further, the compounds of formula (I) wherein $R^5$ is a 1-hydroxyalkyl (i.e., —CO(OH)alkyl) are synthesized by reducing a corresponding compound of formula (I) wherein $R^5$ is a ketone moiety (i.e., —COalkyl) according to the following procedure. The ketone compound of formula (I) is dissolved in an alcoholic solvent and cooled to about 0° C., to which is added sodium borohydride. The mixture is stirred until the bubbling ceases and then stirred at room temperature for approximately 1 hour.

Certain compounds of the formula (I) are synthesized according to the following procedure. To a mixture of N-chlorosuccinimide and pyridine in an inert solvent, such as methylene chloride, is added an oxime of the formula

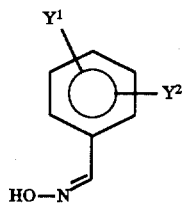

wherein $Y^1$ and $Y^2$ are as defined above for formula (I). The mixture is allowed to stir for about 2 to 5 hours, preferably about 2 hours. A compound of the formula

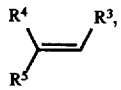

wherein $R^3$, $R^4$ and $R^5$ are as defined above for formula I, is added followed by the addition of triethylamine to the mixture and the mixture stirred for about 2 hours more at room temperature. The reaction is worked up according to methods well known to those skilled in the art.

Compounds of the formula (I) wherein $R^5$ is aminomethyl are synthesized according to the following procedure. A compound of the formula

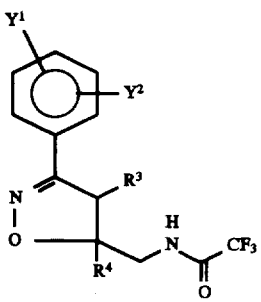

wherein $Y^1$, $Y^2$, $R^3$ and $R^4$ are as defined above for formula (I), is dissolved in a mixture of methanol and water. An inorganic base such as KOH is added to the mixture and the reaction mixture is allowed to stir at room temperature for about 12 to 24 hours, preferably 16 hours. The reaction is worked-up according to methods well-known to those skilled in the art.

Compounds of the formula (I) wherein $R^4$ is —COOH and $R^5$ is an amino group are synthesized according to the following procedure. A compound of the formula

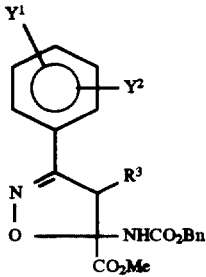

wherein $Y^1$, $Y^2$ and $R^3$ are as defined above for formula (I), is reacted with bromotrimethylsilane for about 12 to 24 hours, preferably 16 hours. Acetonitrile is added, for solubility if necessary, to the reaction mixture and the mixture is heated to reflux until the reaction is substantially complete. The reaction is worked-up according to methods well-known to those skilled in the art.

Compounds of formula (I) wherein $R^5$ is —$(CH_2)_xPO_3H_2$ are synthesized according to the following procedure. A solution of the appropriate phosphonate dissolved in trimethylsilylbromide is stirred for about 2 hours at room temperature. The mixture is evaporated and the residue is diluted with $H_2O$ and an organic solvent such as $CH_2Cl_2$ and stirred for about 2 hours. The mixture is filtered and the aqueous layer is basified with an aqueous inorganic base such as 1N NaOH. The organic layer is discarded and the aqueous layer is washed with additional organic solvent such as $CH_2Cl_2$. The aqueous layer is acidified and extracted with an organic solvent such as EtOAc. Evaporating the EtOAc yields the desired compound.

The synthetic methods outlined above together with the following examples describe methods which were and can be employed to prepare the compounds of this invention.

As ascertained by one skilled in the art enabled by this disclosure, pharmaceutically-acceptable acid addition salts of certain compounds of this invention include, but are not limited to, those formed with HCl, HBr, $HNO_3$, $H_2SO_4$, $H_3PO_4$, $CH_3SO_3H$, p—$CH_3C_6H_4SO_3H$, $CH_3CO_2H$, gluconic acid, tartaric acid, maleic acid and succinic acid. In the case of those compounds of the formula (I) which contain a further basic nitrogen, it will, of course, be possible to form diacid addition salts (e.g., the dihydrochloride) as well as the usual monoacid addition salt. As ascertained by one skilled in the art enabled by this disclosure, pharmaceutically-acceptable cationic salts of certain compounds of this invention include, but are not limited to, those of sodium, potassium, calcium, magnesium, ammonium, N,N'-dibenzylethylenediamine, N-methylglucamine (meglumine), ethanolamine and diethanolamine.

The starting materials and reagents required for the synthesis of the compounds of the present invention are readily available, either commercially, according to literature methods, or by methods exemplified in Preparations below.

The ability of the compounds or the pharmaceutically acceptable salts thereof to inhibit $PDE_{IV}$ and, consequently, demonstrate their effectiveness for treating inflammatory diseases is shown by the following in vitro assay.

BIOLOGICAL ASSAY (Human Lung $PDE_{IV}$)

Thirty to forty grams of human lung tissue is placed in 50 ml of pH 7.4 Tris/phenylmethylsulfonyl fluoride (PMSF)/sucrose buffer and homogenized using a Tekmar Tissumizer® (Tekmar Co., 7143 Kemper Road, Cincinnati, Ohio 45249) at full speed for 30 seconds. The homogenate is centrifuged at 48,000×g for 70 minutes at 4° C. The supernatant is filtered twice through a 0.22 μm filter and applied to a Mono-Q FPLC column (Pharmacia LKB Biotechnology, 800 Centennial Avenue, Piscataway, N.J. 08854) pre-equilibrated with pH 7.4 Tris/PMSF buffer. A flow rate of 1 ml/minute is used to apply the sample to the column, followed by a 2 ml/minute flow rate for subsequent washing and elution. Sample is eluted using an increasing, step-wise NaCl gradient in the Ph 7.4 Tris/PMSF buffer. Eight ml fractions are collected. Fractions are assayed for specific $PDE_{IV}$ activity, determined by [$^3$H]cAMP hydrolysis and the ability of a known $PDE_{IV}$ inhibitor (e.g. rolipram) to inhibit that hydrolysis. Appropriate fractions are pooled, diluted with ethylene glycol (2 ml ethylene glycol/5 ml of enzyme prep) and stored at -20° C. until use.

Compounds are dissolved in DMSO at a concentration of 10 mM and diluted 1:25 in water (400 μM compound, 4% DMSO). Further serial dilutions are made in 4% DMSO to achieve desired concentrations. Final DMSO concentration in the assay tube is 1%. In duplicate the following are added, in order, to a 12×75 mm glass tube (all concentrations are given as final concentrations in assay tube).

i) 25 μl compound or DMSO (1%, for control and blank)

ii) 25 μl pH 7.5 Tris buffer iii) [$^3$H]cAMP (1 μM)

iv) 25 μl $PDE_{IV}$ enzyme (for blank, enzyme is preincubated in boiling water for 5 minutes)

The reaction tubes are shaken and placed in a water bath (37° C.) for 20 minutes, at which time the reaction is stopped by placing the tubes in a boiling water bath for 4 minutes. Washing buffer (0.5 ml, 0.1M 4-(2-hydroxyethyl)-1-piperazineethanesulfonic acid (HEPES)/0.1M NaCl, pH 8.5) is added to each tube on an ice bath. The contents of each tube are applied to an Affi-Gel 601 column (Biorad Laboratories, P.O. Box 1229, 85A Marcus Drive, Melville, N.Y. 11747) (boronate affinity gel, 1 ml bed volume) previously equilibrated with washing buffer. [$^3$H]cAMP is washed with 2×6 ml washing buffer, and [$^3$H]5'AMP is then eluted with 4 ml of 0.25M acetic acid. After vortexing, 1 ml of the elution is added to 3 ml of scintillation fluid in a suitable vial, vortexed and counted for [$^3$H].

% Inhibition is determined by the formula:

$$\% \text{ Inhibition} = 1 - \frac{\text{average cpm (test compound)} - \text{average cpm (blank)}}{\text{average cpm (control)} - \text{average cpm (blank)}} \times 100$$

$IC_{50}$ is defined as that concentration of compound which inhibits 50% of specific hydrolysis of [$^3$H]cAMP to [$^3$H] 5'AMP.

For administration to humans to inhibit $PDE_{IV}$ in the treatment of inflammatory conditions, AIDS, asthma, arthritis, bronchitis, chronic obstructive airways disease, psoriasis, allergic rhinitis, dermatitis and other inflammatory diseases, oral dosages of the compounds are generally in the range of from 0.1–500 mg daily for an average adult patient (70 kg). Thus for a typical adult patient, individual tablets or capsules contain from 0.1 to 50 mg of active compound, in a suitable pharmaceutically acceptable vehicle or carrier. Tablets or capsules can be given in multiple dosages to meet the dosage requirement. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For human use, the compounds of the formula (I) can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic. For topical administration, they are best used in the form of solutions, lotions, ointments, salves and the like.

Thus in a further aspect the invention provides pharmaceutical compositions comprising a compound of the formula (I), or pharmaceutically acceptable salts thereof, together with a pharmaceutically acceptable diluent or carrier.

This invention provides a method of inhibiting $PDE_{IV}$ in a mammal in need thereof which method comprises administering to said mammal an effective amount of a compound of the formula (I) or a pharmaceutically acceptable salt thereof.

This invention further provides a method of treating an inflammatory condition in a mammal in need thereof which comprises administering to said mammal an antiinflammatory amount of a compound of the formula (I) or a pharmaceutically acceptable salt thereof.

Further still, this invention provides a method of treating AIDS, asthma, arthritis, bronchitis, chronic obstructive pulmonary disease, psoriasis, allergic rhinitis, dermatitis or shock in a mammal in need thereof which comprises administering to said mammal an effective amount of a compound or a pharmaceutically acceptable salt thereof.

The present invention is illustrated by the following examples, but it is not limited to the details thereof.

EXAMPLE 1

3-[4-Methoxy-3-(5-phenylpentyloxy)]phenyl-2-isoxazoline-5-carboxylic Acid

To a mixture of 1.00 g (2.43 mmol) of the compound of Preparation 15, 15 ml of MeOH, and 5 ml of water was added 273 mg (4.86 mmol) of KOH. The mixture was stirred overnight at RT and was then partially evaporated to remove MeOH. The residue was diluted with water to a volume of 125 ml, acidified with 6N HCl solution, and extracted with EtOAc (2×125 ml). The combined extracts were dried ($Na_2SO_4$) and evaporated to give 729 mg (78%) of the title compound as an oil. $^1$H NMR (CDCl$_3$): δ 1.44–1.94 (6H, m), 2.64 (2H, t), 3.66–3.70 (2H, m), 3.89 (3H, s), 4.02 (2H, q, J=7), 5.18 (1H, t, J=10), 6.83 (1H, d, J=8), 7.02 (1H, dd, J=8, 2), 7.11–7.31 (6 H, m). FABMS (m/e): 384 (M$^+$+1).

EXAMPLES 2–5

The following compounds were prepared substantially according to the procedure of Example 1.

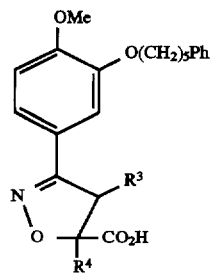

| Example | Ester | R⁴ | R³ | M.P. °C. | Data |
|---|---|---|---|---|---|
| 2 | Compound of Preparation 16 | Me | H | 101–103 | $^1$H NMR(CDCl$_3$): δ 1.40–1.88(6H, m), 1.72(3H, s), 2.58(2H, t, J=7), 3.23(1H, d, J=16), 3.78(1H, d, J=16), 3.93(3H, s), 3.96(2H, q, |

-continued

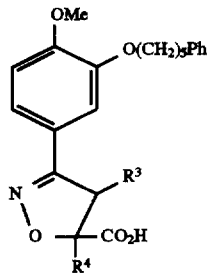

| Example | Ester | R⁴ | R³ | M.P. °C. | Data |
|---|---|---|---|---|---|
| 3 | Compound of Preparation 17 | H | Me* | 101–104 | J=7), 6.76(1H, d, J=8), 6.93(1H, dd, J=8, 2), 7.06–7.22(6H, m) $^1$H NMR(CDCl$_3$): δ 1.41(3H, d, J=7), 1.40–1.88(6H, m), 3.94(3H, s), 3.96–4.01(1H, m), 3.99(2H, q, J=7), 5.00–5.07(1H, m), 6.78(1H, d, J=8), 7.04(1H, d, J=8), 7.10–7.24(6H, m), 7.34(1H, s). FABMS (m/e): 398(M⁺ + 1) |
| 4 | Compound of Preparation 18 | Et | H | 138–140$^b$ | Anal. Calc'd for C$_{24}$H$_{29}$NO$_5$: C, 70.05; H, 7.10; N, 3.40. Found: C, 70.11; H, 7.21; N, 3.42 |
| 5 | Compound of Preparation 19 | Pr | H | 153–155 | Anal. Calc'd for C$_{25}$H$_{31}$NO$_5$: C, 70.56; H, 7.34; N, 3.29. Found: C, 70.49; H, 7.39; N, 3.33 |

*trans stereochemistry
$^b$recrystallized from EtOAc

EXAMPLE 6

(+)-5-Ethyl-3-[4-methoxy-3-(5-phenylpentyloxy)]phenyl-2-isoxazoline-5-carboxylic Acid A mixture of 1.03 g (2.5 mmol) of the compound of Example 4 and 303 mg (2.5 mmol) of (R)-(+)-α-methylbenzylamine were dissolved in 50 ml of MeOH and the solvent was removed. The residual oil crystallized on standing in the refrigerator overnight and was triturated in ether. The solid, 1.17 g, was recrystallized four times from EtOAc to give 340 mg of a fluffy white solid, mp 144°–145° C.; [α]$_D$+26.3° (MeOH). The salt was partitioned between 20 ml of aqueous 1N HCl solution and 40 ml of EtOAc. The organic layer was washed with additional aqueous 1N HCl solution (2×20 ml), dried (MgSO$_4$), and evaporated to 234 mg of a solid. Recrystallization from hexane-EtOAc provided 192 mg of the title compound, mp 122°–124°, [α]$_D$+30.7° (CHCl$_3$). Calc'd. for C$_{24}$H$_{29}$NO$_5$: C, 70.05; H, 7.10; N. 3.48. Found: C, 70.12; H, 6.80; N, 3.32.

EXAMPLE 7

(−)-5-Ethyl-3-[4-methoxy-3-(phenylpentyloxy)]phenyl-2-isoxazoline-5-carboxylic Acid All the mother liquors derived from the (R)-α-methylbenzylamine salt described in Example 6 were combined, concentrated, and partitioned between EtOAc (100 ml) and aqueous 1N HCl solution (50 ml). The organic layer was separated, washed with additional aqueous 1N HCl solution (2×50 ml), dried (MgSO$_4$), and evaporated to 722 mg (1.75 mmol) of a solid. The solid and 212 mg (1.75 mmol) of (S)-(−)-α-methylbenzylamine were dissolved in 30 ml of EtOAc and crystallization was induced by scratching with a glass rod to yield 605 mg of salt. Two recrystallizations from EtOAc gave 483 mg of pure salt, mp 145°–146° C.; [α]$_D$−26.3° (MeOH). The salt was neutralized as described in Example 6 to provide 334 mg of the title compound, mp 122°–123° C. [α]$_D$ −31.0° (CHCl$_3$). Calc'd. for C$_{24}$H$_{29}$NO$_5$: C, 70.05; H 7.10; N, 3.48. Found: C, 70.02; H, 6.85; N, 3.36.

EXAMPLE 8

(−)-3-[4-Methoxy-3-(5-phenylpentyloxy)]phenyl-5-methyl-2-isoxazoline-5-carboxaldehyde To a solution of 290 mg (0.579 mmol) of the compound of Preparation 22 in 20 ml of dry THF at about −78° C. was added dropwise 1.74 ml (1.74 mmol) of a solution of 1M diisobutylaluminum hydride in hexane at such a rate that the reaction temperature was maintained below about −65° C. After about 20 min of stirring the reaction was allowed to warm to RT where TLC analysis indicated the presence of starting material. The mixture was recooled to about −78° C., treated with an additional 0.580 ml of 1M diisobutylaluminum hydride solution, and then allowed to warm to RT. A solution (6 ml) of 1N aqueous HCl was added and the organic layer was extracted with EtOAc (2×50 ml). The combined extracts were dried (MgSO$_4$) and evaporated to 246 mg of a yellow oil. Purification by flash chromatography using a EtOAc-hexane (1:1) eluant gave 137 mg of the title compound as an oil. $^1$H NMR (CDCl$_3$): δ1.28–1.93 (6H, m), 1.58 (3H, s), 2.63 (2H, t, J=7), 3.06 (1H, d, J=16), 3.66 (1H, d, J=16), 3.90 (3H, s), 4.03 (2H, t, J=7), 6.83 (1H, d, J=8), 7.00 (1H, d, J=8), 7.15–7.31 (6H, m) 9.65 (1H, s); MS (m/e): 382 (M⁺+1), 352; [α]$_D$ −35.1° (CHCl$_3$).

EXAMPLES 9–11

The following compounds were prepared substantially according to the procedure of Example 8 substituting the indicated amide for that of Procedure 22.

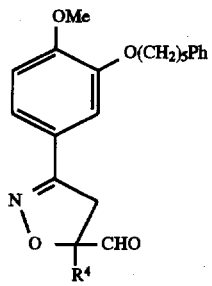

| Example | Amide | R[4] | M.P. °C. | [α]$_D$ (CHCl$_3$) | Data |
|---|---|---|---|---|---|
| 9 | Cmpd of Prep. 24 | Me | oil | +36.6° | MS(m/e): 382(M$^+$ + 1), 352 |
| 10 | Cmpd of Prep. 28 | Pr | oil | −29.4° | $^1$H NMR(CDCl$_3$): δ 0.96(3H, t), 1.39–1.93(10H, m), 2.62 (2H, t, J=8), 3.06(1H, d, J=17), 3.59(1H, d, J=17), 3.86(3H, s), 4.00(3H, t, J=7), 6.83(1H, d, J=8), 7.07(1H, dd, J=8, 2), 7.23–7.30(6H, m), 9.67(1H, s) |
| 11 | Cmpd of Prep. 27 | Pr | oil | +37.1° | MS(m/e): 410(M$^+$ + 1), 382 |

EXAMPLE 12

5-Hydroxy-3-[4-methoxy-3-(5-phenylpentyloxy)]phenyl-2-isoxazoline

To a solution of 500 mg (1.26 mmol) of the compound of Preparation 29 in 15 ml of MeOH was added 0.50 ml (1.50 mmol) of 3M NaOMe solution in MeOH. After stirring for about 1 hr at RT, the mixture was evaporated and the residue was diluted with 10 ml of ice water. The mixture was acidified with aqueous 6M HCl solution, extracted with EtOAc (2×50 ml), washed with brine (50 ml), dried (Na$_2$SO$_4$), and evaporated to 307 mg of an oil. Purification by flash chromatography using a EtOAc-hexane (1:1) eluant afforded 307 mg of the title compound, mp 89°–91° C. Anal. Calc'd. for C$_{20}$H$_{25}$NO$_4$: C, 70.96; H, 7.09; N, 3.93. Found: C, 70.86; H, 7.10; N, 3.97.

EXAMPLE 13

(+)-5-Hydroxymethyl-3-[4-methoxy-3-(5-phenylpentyloxy)]phenyl-2-isoxazoline

To a solution of 300 mg (0.617) of the compound of Preparation 20 in 10 ml of dry THF chilled to about −78° C. was added dropwise 1.85 ml (1.85 mmol) of 1M diisobutylaluminum hydride solution in hexane. After stirring for 20 min at about −78° C., the mixture was allowed to warm to about −20° C. and was quenched with 4 ml of aqueous 1N HCl solution. The mixture was concentrated, dissolved in 30 ml of EtOAc, washed with water (2×30 ml), dried (MgSO$_4$), and evaporated to 200 mg of a brown oil.

A solution of 184 mg of the oil above in 3 ml of MeOH was treated with 19 mg (0.50 mmol) of sodium borohydride, and the mixture was allowed to stir at RT for about 16 h. The mixture was quenched with aqueous 1N HCl solution and was partially evaporated to remove MeOH. The residue was extracted with EtOAc (1×50 ml) and the organic layer was separated, washed with water, dried (MgSO$_4$), and evaporated to a brown oil. Purification by flash chromatography (10 g of silica gel) using a EtOAc-hexane (2:3) eluant afford 96 mg of the title compound as an oil. $^1$H NMR (CDCl$_3$): δ 1.46–1.92 (6H, m), 2.62 (3H, t, J=8), 3.18–3.39 (2H, m), 3.63–3.90 (2H, m), 3.86 (3H, s), 4.80–4.85 (1H, m), 6.83 (1H, d, J=8), 7.02 (1H, dd, J=8, 2), 7.12–7.33 (6H, m), MS (m/e): 370 (M$^+$+1). [α]$_D$ +58.0° (CHCl$_3$).

EXAMPLE 14

(−)-5-Hydroxymethyl-3-[4-methoxy-3-(5-phenylpentyloxy)]phenyl-2-isoxazoline

The title compound was prepared substantially according to the procedure of Example 13 substituting the compound of Preparation 21 for the compound of Preparation 20. [α]$_D$ −60.0° (CHCl$_3$).

EXAMPLE 15

(+)-5-Hydroxymethyl-3-[4-methoxy-3-(5-phenylpentyloxy)]phenyl-5-methyl-2-isoxazoline A solution of 200 mg (0.524 mmol) of the compound of Example 9 in 4 ml of MeOH was treated with 18 mg (0.524 mmol) of sodium borohydride and the mixture was stirred for about 16 h at RT. The mixture was quenched with aqueous 1N HCl solution and was partially evaporated to remove MeOH. The residue was diluted with 50 ml of water, extracted with EtOAc (2×50 ml), dried (MgSO$_4$), and evaporated to 194 mg of an oil. Crystallization of the oil from hexane-ether (3:1) afforded 131 mg of the title compound, mp 76°–78° C. [α]$_D$ +34.7° (CHCl$_3$). Anal. Calc'd for C$_{23}$H$_{29}$NO$_4$•¼H$_2$O: C, 71.14; H, 7.60; N. 3.61. Found: C, 71.51; H, 7.72; N, 3.71.

EXAMPLE 16

(−)-5-Hydroxymethyl-3-[4-methoxy-3-(5-phenylpentyloxy)]phenyl-5-methyl-2-isoxazoline The title compound was prepared substantially according to the procedure of Example 15 substituting the compound of Example 8 for the compound of Example 9, mp 86°–88° C. [α]$_D$ −38.2° (CHCl$_3$). Anal. Calc'd. for C$_{23}$H$_{29}$NO$_4$•¼H$_2$O: C, 71.14; H, 7.60; N. 3.61. Found: C, 71.51; H, 7.72; N, 3.71.

EXAMPLE 17

(+/−)-5-Hydroxymethyl-3-[4-methoxy-3-(5-phenylpenytyloxy)]phenyl-5-methyl-2-isoxazoline To a solution of 200 mg (0.47 mmol) of the compound of Preparation 16 in 5 ml of THF chilled to about −78° C. was added dropwise 1.03 ml (1.03 mmol) of 1.0M diisobutylaluminum hydride solution in hexane. The mixture was allowed to warm to about 0° C. where TLC analysis indicated the presence of starting material. After rechilling to about −78° C., an additional 1.03 ml of a 1.0M diisobutylaluminum hydride solution in hexane was added and the mixture was allowed to warm to about −30° C. The mixture was quenched with aqueous 1N HCl solution and after warming to RT was extracted with EtOAc (2×25 ml). The combined organic layers were dried (MgSO$_4$) and evaporated to 199 mg of a yellow oil. Purification of the oil by flash chromatography (15 g of silica gel) using a EtOAc-hexane eluant (3:2) afforded 163 mg of an oil which spontaneously crystallized upon standing. Trituration with hexane-ether (3:1) afforded 69 mg of the title compound, mp 67°–69° C. $^1$H NMR (CDCl$_3$): δ1.39 (3H, s), 1.41–1.94 (6H, m), 2.61 (2H, t, J=8), 2.96 (1H, d, J=16), 3.44 (1H, d, J=16), 3.49–3.72(2H, m), 3.85 (3H, s), 4.00 (2H, t, J=7), 6.82 (1H, d, J=9), 6.99 (1H, dd, J=2, 9), 7.14–7.32 (6H, m). FABMS (m/e): 384 (M$^+$+1).

EXAMPLE 18

(+)-5-Ethyl-5-hydroxymethyl-3-[4-methoxy-3-(5-phenylpentyloxy)]phenyl-2-isoxazoline The title compound was prepared as an oil substantially according to the procedure of Example 13 substituting the compound of Preparation 25 for the compound of Preparation 20. $^1$H NMR (CDCl$_3$): δ 0.98 (3H, t, J=7), 1.52–1.93 (8H, m), 2.35–2.70 (1H, bd s), 2.65 (2H, t, J=7), 3.06 (1H, d, J=17), 3.36 (1H, d, J=17), 3.60 (1H, d, J=12), 3.75 (1H, d, J=12), 3.89 (3H, s), 4.04 (2H, t, J=7), 6.85 (1H, d, J=8), 7.04 (1H, dd, J=2, 8), 7.18–7.35 (6H, m). MS (m/e): 397, 362, 310, 91 (base). [α]$_D$ +20.1° (CHCl$_3$).

EXAMPLE 19

(−)-5-Ethyl-5-hydroxymethyl-3-[4-methoxy-3-(5-phenylpentyloxy)]phenyl-2-isoxazoline The title compound was prepared as an oil substantially according to the procedure of Example 13 substituting the compound of Preparation 26 for the compound of Preparation 20. [α]$_D$ −16.3° (CHCl$_3$).

EXAMPLES 20–21

The following compounds were prepared as oils substantially according to the procedure of Example 15 substituting the indicated aldehyde for the compound of Example 9.

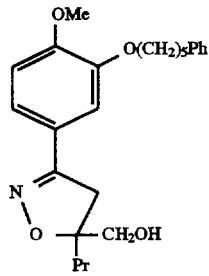

| Ex. | Aldehyde | [α]$_D$ (CHCl$_3$) | $^1$H NMR(CDCl$_3$): |
|---|---|---|---|
| 20 | Cmpd of Ex. 11 | +8.9° | δ 0.93(3H, t, J=7), 1.36–1.90 (10H, m), 2.62(2H, t, J=8), 3.03(1H, d, J=17), 3.34(1H, d, J=17), 3.52–3.74(2H, m), 3.86(3H, s), 4.01(2H, t, J=7), 6.82(1H, d, J=8), 7.01(1H, dd, J=2, 8), 7.15–7.32(6H, m) |
| 21 | Cmpd of Ex 10 | −9.8° | MS(m/e): 412(M$^+$ + 1), 382, 312 |

EXAMPLES 22–28

The following compounds were prepared substantially according to the procedure of Preparation 15 substituting the indicated olefin for ethyl acrylate.

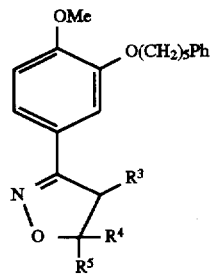

| Ex | R$^5$ | R$^4$ | R$^3$ | Olefin | M.P. °C. | Data |
|---|---|---|---|---|---|---|
| 22 | H | H | H | CH$_2$=CH$_2$ | 103–105 | Anal. Calc'd. for C$_{21}$H$_{25}$NO$_3$.¼H$_2$O: C, 73.33; H, 7.32; N, 4.07. Found: C, 73.56; H, 7.20; N, 4.13 |
| 23 | Me | Me | H | Me$_2$C=CH$_2$ | 83–85 | Anal. Calc'd. for C$_{23}$H$_{29}$NO$_3$.¼H$_2$O: C, 74.26; H, 7.85; N, 3.36. Found: C, 74.56; H, 7.90; N, 3.84 |
| 24 | COCH$_3$ | H | H | CH$_2$=CHCOCH$_3$ | oil | $^1$H NMR(CDCl$_3$): δ 1.46–1.90(6H, m), |

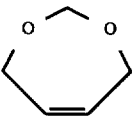

| Ex | $R^5$ | $R^4$ | $R^3$ | Olefin | M.P. °C. | Data |
|---|---|---|---|---|---|---|
| 25 | $CONH_2$ | H | H | $CH_2=CHCONH_2$ | 152–154 | 2.35(3H, s), 2.62(2H, t, J=8), 3.39–3.62(2H, m), 3.86(3H, s), 4.01 (2H, t, J=7), 4.97(1H, dd, J=6, 11), 6.83 (1H, d, J=8), 7.03 (1H, dd, J=2, 8), 7.15–7.33(6H, m) Anal. Calc'd for $C_{22}H_{26}N_2O_4$: C, 69.08; H, 6.85; N, 7.32. Found: C, 68.80; H, 6.64; N, 7.26 |
| 26 | $(CH_2)_2OH$ | H | H | $CH_2=CH(CH_2)_2OH$ | 84–86 | $^1H$ NMR($CDCl_3$): δ 1.40–1.81(8H, m), 2.59(2H, t, J=7), 3.05 (1H, dd, J=8, 17), 3.43(1H, dd, J=10, 17), 3.52(2H, q, J=5), 3.77(3H, s), 3.96(2H, t, J=6), 4.56(1H, t, J=5), 4.70–4.75(1H, m), 6.98(1H, d, J=8), 7.12–7.29(7H, m), MS (m/e): 384($M^+$ + 1) |
| 27 | H | $-CH_2OCH_2OCH_2-$* | | (structure) | 122–125 | $^1H$ NMR($CDCl_3$): δ 1.48–1.89(6H, m), 2.62(2H, t, J=8), 3.86 (3H, s), 3.91–4.40(8H, m), 4.69(1H, d, J=6), 4.87(1H, d, J=6), 6.86(1H, d, J=8), 7.03(1H, dd, J=2, 8), 7.17–7.32(6H, m), MS (m/e): 412($M^+$ + 1) |
| 28 | $CH_2NHCOCF_3$ | H | H | Preparation 14 | 91–94 | $^1H$ NMR($CDCl_3$): δ 1.39–1.94(6H, m), 2.56(2H, t, J=7), 2.95 (1H, dd, J=8, 16) 3.17 (1H, dd, J=12, 16), 3.17–3.48(1H, m), 3.60–3.68(1H, m), 3.91(3H, s), 3.95(2H, t, J=7), 4.72–4.82(1H, m), 6.64(1H, bd s), 6.75(1H, d, J=8), 6.92(1H, dd, J=2, 8) 7.07–7.22(6H, m). FABMS(m/e): 465 ($M^+$ + 1) |

*cis stereochemistry in the ring junction

EXAMPLE 29

5-Aminomethyl-3-[4-methoxy-3-(5-phenylpentyloxy)]phenyl-2-isoxazoline Hydrochloride A mixture of 250 mg (0.538 mmol) of the compound of Example 28, 5 ml of MeOH, and 1 ml of water was treated with 91 mg (1.62 mmol) of KOH and was allowed to stir for about 16 h at RT. The mixture was partially evaporated to remove MeOH and the residue was diluted with EtOAc (50 ml) and sat'd. aqueous $NaHCO_3$ solution (50 ml). The organic layer was separated and washed with an additional 50 ml of sat'd. aqueous $NaHCO_3$ solution, dried ($MgSO_4$), and evaporated to an oil. NMR analysis indicated the presence of a small amount of starting material, so the oil was treated again as described above using 30 mg of KOH.

After work-up 126 mg of an oil was obtained, which was treated with HCl gas in 3 ml of $CHCl_3$. The solvent was evaporated and the semi-solid residue was triturated in ether to yield 70 mg of the title compound, mp 106°–109° C. Anal. Calc'd for $C_{22}H_{28}N_2O_3 \cdot HCl$: C, 63.78; H, 7.00; N, 6.76. Found: C, 63.93; H, 7.29; N, 6.65.

EXAMPLE 30

5-Amino-3-[4-methoxy-3-(5-phenylpentyloxy)] phenyl-2-isoxazoline-5-carboxylic Acid Hydrobromide A mixture of 50 mg (0.094 mmol) of the compound of Preparation 30 and 2 ml of bromotrimethylsilane was stirred for about 16 hr at RT. A precipitate was observed and a small amount of acetonitrile was added and the mixture was heated to reflux. The mixture was evaporated and the residue was triturated with ether to afford 57 mg of the title compound, mp 123°–127° C. $^1$H NMR ($CD_3OD$): δ 1.47–1.88 (6H, m), 2.64 (2 H, t, J=7), 3.82 (1H, d, J=17), 3.88 (3H, s), 4.02 (2H, t, J=8), 4.29 (1 H, d, J=17), 7.03 (1H, d, J=8), 7.12–7.33 (7H, m). FABMS (m/e): 477, 399.

EXAMPLES 31–32

Racemic Diastereomers of 5-(1-Hydroxyethyl)-3-[4-methoxy-3-(5-phenylpentyloxy)]phenyl-2-isoxazoline To a solution of 360 mg (0.944 mmol of the compound of Example 24 in 4 ml of MeOH chilled to about 0° C. was added 36.0 mg (0.944 mmol of $NaBH_4$. After the bubbling ceased, the ice bath was removed and stirring was continued for about 1 h. Excess aqueous 1N HCl solution was added and the mixture was partially evaporated to remove MeOH. The residue was diluted with 50 ml of water and extracted with EtOAc (2×50 ml). The combined EtOAc extracts were dried ($MgSO_4$) and evaporated to 360 mg of an oil, which was separated by flash chromatography (50 g of silica gel) using ether-hexane (7:3) and ether as eluants. The fractions containing the less polar diastereomer ($R_f$ 0.28, ether) were combined and evaporated to 31 mg of an oil which was crystallized from hexane, mp 102°–103° C. Anal. Calc'd for $C_{23}H_{29}NO_4$: C, 72.04; H, 7.62; N, 3.65. Found: C, 72.22; H, 7.57; N, 3.41.

The fractions containing the more polar diastereomer ($R_f$ 0.23, ether) were combined and evaporated to 117 mg of an oil which was crystallized from hexane, mp 72°–74° C. Anal. Calc'd for $C_{23}H_{29}NO_4$: C, 72.04; H, 7.62; N, 3.65. Found: C, 72.26; H, 7.57; N, 3.50.

EXAMPLES 33–36

The following compounds were prepared by saponification of the indicated ester, substantially according to the procedure of Example 1.

| Ex. | $R^2$ | $R^4$ | Ester | M.P. °C. | Data |
|---|---|---|---|---|---|
| 33 | cyclopentyl | H | Cmpd. of Prep. 31 | 135–137 | Anal. Calc'd for $C_{16}H_{19}NO_5$: C, 62.94; H, 6.27; N, 4.59. Found: C, 62.82; H, 6.01; N, 4.59. |
| 34 | cyclopentyl | Me | Cmpd. of Prep. 32 | 149–151 | Anal. Calc'd for $C_{17}H_{21}NO_5 \cdot \frac{1}{4}H_2O$: C, 62.99; H, 6.64; N, 4.32. Found: C, 63.22; H, 6.38; N, 4.32. |
| 35 | $(CH_2)_4Ph$ | H | Cmpd. of Prep. 35 | 108–110 | $^1$H NMR(DMSO-$d_6$): δ 1.60–1.75(4H, m), 2.64(2H, t, J=6), 3.50–3.72(2H, m), 3.78 (3H, s), 3.99(2H, t, J=6), 5.11(1H, dd, J=3, 11), 6.99 (1H, d, J=8), 7.16–7.30(7H, m). |

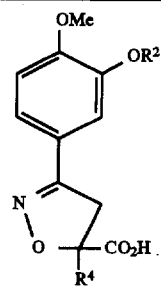

| Ex. | R² | R⁴ | Ester | M.P. °C. | Data |
|---|---|---|---|---|---|
| 36 | (S)-(+)-exo | H | Cmpd. of Prep. 33 | oil | ¹H NMR(CDCl₃): δ 1.10–1.82 (8H, m), 2.28(1H, s), 2.49 (1H, d, J=2), 3.65–3.70(2H, m), 3.85(3H, s), 4.20(1H, d, J=4), 5.18(1H, dd, J=5, 12), 6.82(1H, d, J=8), 7.01(1H, d, J=8), 7.27(1H, s). |

EXAMPLE 37

3-(3-Cyclopentyloxy-4-methoxy)phenyl-2-isoxazoline-5-carboxaldehyde

To a solution of 250 mg (0.750 mmol) of the compound of Preparation 31 in 5 ml of THF chilled to about −78° C. was added dropwise 1.88 ml (1.88 mmol) of a 1M diisobutylaluminum hydride solution in hexane. The mixture was stirred for about 30 min at about −78° C. and was quenched by the addition of 3 ml of MeOH. Following the addition of 10 ml of 1N aqueous HCl solution, the mixture was allowed to warm to RT and was partially evaporated to remove THF and MeOH. The residue was extracted with EtOAc (2×50 ml) and the combined extracts were washed with sat'd. aqueous NaHCO₃ (2×30 ml), dried (Na₂SO₄), and evaporated to 205 mg of an oil. Purification of the oil by flash chromatography (50 g of silica gel) using an EtOAc-hexane (1:1 to 3:1) eluant afforded 173 mg of the title compound as an oil. The NMR spectrum indicated partial hydration of the aldehyde. ¹H NMR (CDCl₃): δ 1.50–2.05 (8H, m), 3.20–3.62 (2.5H, m), 3.83 and 3.84 (3H, two s), 4.66–4.85 (1.5H, m), 4.98–5.07 (1H, m), 6.84 (1H, d, J=8), 7.04 (1H, dd, J=2, 8), 7.35 (1H, d, J=2), 9.80 (0.5H, s).

EXAMPLE 38

3-[-3-(S)-(exo)-Bicyclo[2.2.1]hept-2-yloxy-4-methoxy]phenyl-5-methyl-2-isoxazoline-5-carboxaldehyde The title compound was prepared as an oil by diisobutylaluminum hydride reduction of the compound of Preparation 34, substantially according to the procedure of Example 8. ¹H NMR (CDCl₃): δ 1.10–1.82 (8H, m), 1.56 (3H, s), 2.25–2.50 (1 H, m), 2.49 (1H, d, J=1), 3.06 (1H, d, J=17), 3.65 (1H, d, J=17), 3.84 (3H, s), 4.11 (1H, d, J=6), 6.81 (1H, d, J=6), 6.98 (1H, dd, J=2, 8), 7.27 (1H, d, J=2), 9.67 (1H, s). MS (m/e): 330 (M⁺+1). [α]_D −24.3° (CHCl₃).

EXAMPLES 39 and 40

The following compounds were prepared as oils by NaBH₄ reduction of the indicated aldehydes, substantially according to the procedure of Example 15.

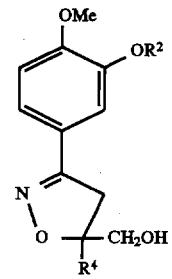

| Ex | R² | R⁴ | Aldehyde | [α]_D (CHCl₃) | Data |
|---|---|---|---|---|---|
| 39 | cyclopentyl | H | Cmpd. of Example 37 | — | ¹H NMR(CDCl₃): δ 1.50–2.05 (8H, m), 3.15–3.36(2H, m), 3.60–3.85(2H, m), 3.94(3H, s), 3.73–3.85(2H, m), 6.79 (1H, d, J=8), 6.98(1H, dd, J=2, 8), 7.30(1H, d, J=2). FABMS(m/e): 292(M⁺ + 1) |

-continued

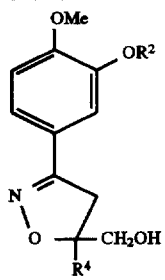

| Ex | R² | R⁴ | Aldehyde | [α]_D (CHCl₃) | Data |
|----|----|----|----------|---------------|------|
| 40 | (S)-(+)-exo (norbornyl) | Me | Cmpd. of Example 38 | −4.8° | ¹H NMR(CDCl₃): δ 1.10–1.82 (m, 8H), 1.39(3H, s), 1.97(1H, dd, J=5, 6), 2.24–2.28(1H, m), 2.49(1H, d, J=4), 2.97(1H, d, J=17), 3.43(1H, d, J=17), 3.52–3.73(2H, m), 3.84(3H, s), 4.21(1H, d, J=7), 6.81 (1H, d, J=8), 7.10(1H, dd, J=2, 8) 7.28(1H, d, J=2). FABMS(m/e): 332(M⁺ + 1) |

EXAMPLE 41

3-[4-Methoxy-3-(5-phenylpentyloxy)]phenyl-2-isoxazolin-5-ylphosphonic Acid

A solution of 50 mg of the compound of Preparation 38 in 1 ml of trimethylsilyl-bromide was stirred for about 2 h at RT. The mixture was evaporated and the residue was diluted with water (4 ml) and CH₂Cl₂ (3 ml) and was stirred for about 2 h. The mixture was filtered and the aqueous layer was basified with aqueous 1N NaOH solution. The organic layer was separated and the aqueous layer was washed with additional CH₂Cl₂ (2×15 ml). Acidification of the aqueous layer with aqueous 1N HCl solution, extraction with EtOAc (2×15 ml), drying (MgSO₄), and evaporation afforded 42 mg of the title compound as an oil. ¹H NMR (DMSO-d₆): d 1.37–1.78 (6H, m), 2.58 (2H, t, J=7), 3.57–3.77 (2H, m), 3.89 (3H, s), 3.96 (2H, t J=7), 4.61 (1H, t, J=10), 7.97 (1H, d, J=8), 7.08–7.26 (7H, m), FABMS (m/e): 420 (M⁺+1).

EXAMPLES 42–45

The following compounds were prepared in an analogous manner to the procedure of Example 41 using as starting material the compounds from the indicated Preparations.

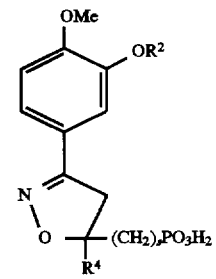

| Ex | R² | R⁴ | s | Cmpd of Prep | M.P. °C. | Data |
|----|----|----|---|--------------|----------|------|
| 42 | (CH₂)₅Ph | Me | 0 | 39 | 175–177* | Calc'd. for C₂₂H₂₈NO₆P.H₂O: C, 58.53; H, 6.65; N, 3.10. Found: C, 58.27; H, 6.61; N, 3.16 |
| 43 | (CH₂)₄Ph | H | 1 | 40 | 137–139 | Calc'd. for C₂₂H₂₈NO₆P.¼H₂O: C, 60.28; H, 6.51; N, 3.20. Found: C, 60.17; H, 6.32; N, 3.19 |
| 44 | (CH₂)₅Ph | Me | 1 | 41 | 112–115* | Calc'd. for C₂₃H₃₀NO₆P.H₂O: C, 59.29; H, 6.87; N, 3.00. Found: C, 58.99; H, 6.94; N, 2.97 |

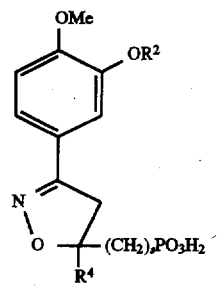

| Ex | R² | R⁴ | s | Cmpd of Prep | M.P. °C. | Data |
|---|---|---|---|---|---|---|
| 45 | cyclopentyl | H | 0 | 42 | 166–168 | ¹H NMR(DMSO-d₆): d 1.50–1.90 (8H, m), 3.22–3.70(2H, m), 3.73 (3H, s), 4.56(1H, t, J=12), 4.72–4.80(1H, m), 6.93(1H, d, J=8), 7.09(1H, d, J=8), 7.16(1H, s) |

*recrystallized from EtOAc

PREPARATION 1

4-Methoxy-3-(5-phenylpentyloxy)benzaldehyde Oxime

A mixture of 25.0 g (0.164 mol) of isovanillin, 26.9 g (0.164 mol) of 5-phenyl-1-pentanol, 64.5 g (0.246 mol) of triphenylphosphine and 250 ml of THF was treated dropwise with 42.8 g (0.246 mol) of diethyl azodicarboxylate. The mixture was heated to about 90° C. for about 6 h and then stirred overnight at RT. The solvent was evaporated and the residue was diluted with 500 ml of EtOAc, washed with water (1×400 ml), 1N NaOH solution (2×400 ml), brine (1×400 ml), dried (MgSO₄), and evaporated to 119 g of a brown oil. Purification by flash chromatography (750 g of silica gel) using an EtOAc-hexane (3:7) eluant afforded 29.8 g (61%) of the title compound as an oil. ¹H NMR (CDCl₃): δ 1.42–1.92 (6H, m), 2.61 (2H, t, J=7), 3.91 (3H, s), 4.03 (2H, t, d=7), 6.91 (1H, d, J=8), 7.10–7.40 (m, 7H), 9.77 (s, 1H)

To a solution of 29.8 g (0.100 mol) of the aldehyde above in 300 ml of 95% ethanol was added 13.7 g (0.197 mol) of hydroxylamine hydrochloride in 100 ml of water followed by 16.6 g (0.197 mol) of sodium bicarbonate in small portions (gas evolution!). The mixture was stirred for about 4 h at RT and the ethanol was removed by evaporation. The residue was diluted with 250 ml of water and extracted with EtOAc (2×200 ml). The combined extracts were dried (MgSO₄) and evaporated to a yellow oil which was crystallized from hexane/ether to afford 15.0 g of the title compound, mp 65°–67° C. ¹H NMR (CDCl₃): δ 1.46–1.93 (6H, m), 2.62 (2H, t, J=7), 3.88 (3H, s), 4.02 (2H, t, J=7), 6.99–7.62 (m, 6H), 7.49 (1H, s), 8.04 (1H, s).

An additional 2.00 g of product was obtained as a second crop from the filtrate, mp 67°–69° C. Evaporation of the filtrate and purification of the residue by flash chromatography using an EtOAc-hexane (2:3) eluant also provided an additional 4.18 g of product, mp 64°–66° C.

PREPARATIONS 2–4

Reaction of the appropriate alcohol with isovanillin and condensation of the resulting aldehyde with hydroxylamine hydrochloride, substantially according to the procedure of Preparation 1, afforded the following compounds as oils.

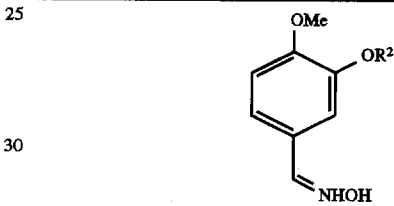

| Prep. # | R² | ¹H NMR CDCl₃, δ |
|---|---|---|
| 2 | (CH₂)₄Ph | 1.70–1.90(m, 4H), 2.65(2H, t, J=7), 3.95(3H, s), 4.10(2H, t, J=7), 6.90(1H, d, J=8), 6.94–7.26(6H, m), 6.97(1H, dd, J=2, 8), 7.56(1H, s), 8.01(1H, s) |
| 3 | cyclopentyl | 1.50–2.02(8H, m), 3.94(3H, s), 4.62–4.80(1H, m), 6.91(1H, d, J=8), 6.97(1H, dd, J=8 and 1), 7.17(1H, d, J=1), 8.02(1H, s), 8.16(1H, s) |
| 4 | ![norbornyl] (S)-(+)-exo | 1.10–1.80(8H, m), 2.26–2.32(1H, m), 2.47–2.52(1H, m), 3.84(3H, s), 4.21(1H, d, J=7), 6.82(1H, d, J=8), 6.98(1H, dd, J=8 and 2), 7.13(1H, d, J=2), 7.78(1H, s), 8.03(1H, s) |

PREPARATION 5

Ethyl 2-Methylenebutyrate

A mixture of 5.0 g (0.019 mol) of triethyl 2-phosphonobutyrate, 5.5 g (0.039 mol) of K₂CO₃, 6.2 g (0.076 mol) of 37% aqueous formaldehyde solution, and 15 ml of water was heated to about 80° C. for about 45 min. After cooling to RT, 75 ml of ether was added and the organic layer was separated, washed with brine (1×20 ml), dried (MgSO₄), and filtered. The ether was carefully removed by distillation, leaving behind 2.1 g (87%) of the title compound as a clear oil which was used directly without further purification. ¹H NMR (CDCl₃): δ 1.01 (3H, t, J=7), 1.24 (3H, t, J=7), 2.26 (2H, q, J=7) 4.14 (2H, q, J=7), 5.45 (1H, s), 6.06 (1H, s).

PREPARATION 6

Ethyl 2-Methylenepentanoate

Reaction of triethyl 2-phosphonopentanoate, substantially according to the procedure of Preparation 5, gave the title compound as an oil. $^1$H NMR (CDCl$_3$): δ 1.05 (3H, t, J=7), 1.28 (3H, t, J=7), 1.41–1.53 (2H, m), 2.87 (2H, q, J=7), 4.18 (2H, q, J=7), 5.49 (1H, s), 6.11 (1H, s).

PREPARATION 7

2-Methylenebutyric Acid

To a solution of 5.08 g (39.6 mmol) of the compound of Preparation 5 in 95 ml of EtOH and 40 ml of water was added 1.58 g (39.6 mmol) of solid NaOH, and the mixture was stirred for about 2 h at RT. An additional 0.15 g of NaOH was added and stirring was continued for about 2 h. The mixture was partially evaporated to remove the EtOH and the residue was diluted with 20 ml of H$_2$O and acidified to pH 2 with aqueous 6N HCl solution. Extraction with EtOAc, drying (MgSO$_4$), and evaporation afforded 2.49 g (63%) of the title compound as an oil. $^1$H NMR (CDCl$_3$): δ 1.11 (3H, t, J=7), 2.34 (2H, q, J=7), 5.66 (1H, s), 6.30 (1H, s), 11.78 (1H, bd s).

PREPARATION 8

2-Methylenepentanoic Acid

Reaction of the compound of Preparation 6, substantially according to the procedure of Preparation 7, gave the title compound as an oil. $^1$H NMR (CDCl$_3$): δ 0.91 (3H, t, J=7), 2.40–2.54 (2H, m), 2.26 (2H, t, J=7), 5.62 (1H, s), 6.27 (1H, s).

PREPARATION 9

(S)-(−)-(N-α-Methylbenzyl)acrylamide

To a solution of 5.0 g (0.055 mol) of acryloyl chloride in 30 ml of CH$_2$Cl$_2$ chilled to about 0° C. was added dropwise 7.1 ml (6.7 g, 0.055 mol) of (S)-(−)-α-methylbenzylamine. After the exotherm had subsided, 8.5 ml (6.2 g, 0.061 mol) of triethylamine was added dropwise and the mixture was allowed to warm to RT. Following about 2 h of additional stirring, the solvent was removed by evaporation and the residue was taken up in 200 ml of EtOAc and washed with aqueous 1N HCl solution, aqueous sat'd. NaHCO$_3$ solution, dried (MgSO$_4$), and evaporated to a solid. Trituration in hexane-ether afforded 7.8 g of the title compound as a solid, mp 97°–99° C. $^1$H NMR (CDCl$_3$): δ 1.50 (3H, d, J=7), 5.11–5.21 (1H, m), 5.63 (1H, dd, J=2, 10), 5.77 (1H, bd s), 6.06 (1H, dd, J=10, 13), 6.26 (1H, dd, J=1, 17), 7.19–7.32 (5H, m).

PREPARATION 10

(S)-(−)-(N-α-Methylbenzyl)-2-methylpropionamide

To a solution of 5.00 g (0.0581 mol) of methacrylic acid in 100 ml of THF was added 7.03 g (0.0581 mol) of (S)-(−)-α-methylbenzylamine, 7.84 g (0.0581 mol) of hydroxybenztriazole, and 11.1 g (0.0581 mol) of 1-(3-dimethylaminopropyl)-3-ethylcarbodiimide hydrochloride. After stirring for about 4 h at RT, the solvent was removed by evaporation and the residue was taken up in 200 ml of EtOAc and washed with water (2×100 ml), aqueous 1N HCl solution (2×100 ml), sat'd. aqueous NaHCO$_3$ solution, dried (MgSO$_4$), and evaporated to solid. Trituration in hexane-ether (2:1) afforded 8.68 g of the title compound as a white solid, mp 95°–98° C. $^1$H NMR (CDCl$_3$): δ 1.51 (3H, d, J=7), 1.93 (3H, s), 5.09–5.19 (1H, m), 5.29 (1H, s), 5.65 (1H, s), 5.95 (1H, bd s), 7.20–7.34 (5H, m).

PREPARATIONS 11–13

Reaction of the appropriate acid with (R)-(+)-α-methylbenzylamine, substantially according to the procedure of Preparation 10, afforded the following compounds.

| Prep. # | Q | Acid | M.P. °C. | $^1$H NMR CDCl$_3$, δ |
|---|---|---|---|---|
| 11 | Me | Methacrylic acid | 93–95 | 1.53(3H, d, J=7), 1.97(3H, s), 5.10–5.23 (1H, m), 5.23(1H, s), 5.64(1H, s), 6.01(1H, bd s), 7.25–7.37(5H, m) |
| 12 | Et | Cmpd of Prep 7 | oil | 1.07(3H, t, J=7), 1.53(3H, d, J=7), 2.34 (2H, q, J=7), 5.13–5.25(1H, m), 5.26(1H, s), 5.59(1H, s), 6.06(1H, bd s), 7.20–7.35 (5H, m) |
| 13 | Pr | Cmpd of Prep 8 | 69–71 | 0.91(3H, t, J=7), 1.29–1.54(2H, m), 1.53 (3H, d, J=8), 2.28(2H, t, J=8), 5.12–5.22 1H, m), 5.24(1H, s), 5.57(1H, s), 5.96(1H, bd s), 7.25–7.36(5H, m) |

PREPARATION 14

(N-Trifluoroacetyl)allylamine

A solution of 9.97 g (0.175 mol) of allylamine in 100 ml of pyridine chilled to about 0° C. was treated dropwise with 37.2 g (0.175 mol) of trifluoroacetic anhydride. After about 2 h of stirring the solvent was removed by evaporation. The residue was taken up in 200 ml of CH$_2$Cl$_2$ and washed with aqueous 1N HCl solution (2×100 ml), sat'd. aqueous NaHCO$_3$ solution, dried (Na$_2$SO$_4$), and evaporated to give 18.9 g (79%) of the title compound as an oil. $^1$H NMR (CDCl$_3$): d 3.97 (2H, t, J=5), 5.20 (1H, s), 5.27 (1H, d, J=10), 5.74–5.88 (1H, m), 6.57 (1H, bd s).

PREPARATION 15

3-[4-Methoxy-3-(5-phenylpentyloxy)]phenyl-2-isoxazoline-5-carboxylic Acid Ethyl Ester To a mixture of 1.28 g (9.57 mmol) of N-chlorosuccinimide, 200 μl of pyridine, and 200 ml of CH$_2$Cl$_2$ was added 2.00 g (6.38 mmol) of the compound of Preparation 1 in a solution of 15 ml of $CH_2Cl_2$. An exotherm was observed after about 10 min and following about 2 h of stirring at RT, 644 mg (698 µl, 6.38 mmol) of ethyl acrylate was added followed by 966 mg (1.33 ml, 9.57 mmol) of triethylamine. After the exotherm subsided, the mixture was stirred for about 2 h at RT. The mixture was diluted with 250 ml of $CH_2Cl_2$ and washed with aqueous 1N HCl solution, sat'd. aqueous $NaHCO_3$ solution, dried ($Na_2SO_4$), and evaporated to an oil. Purification by flash chromatography (100 g of a silica gel) using an EtOAc-hexane (2:3) eluant afforded 1.82 g (69%) of the title compound as an oil. $^1$H NMR ($CDCl_3$): δ 1.29 (3H, t, J=7), 1.40–1.91 (6H, m), 2.60 (2H, t, J=7), 3.55–3.58 (2H, m), 3.95 (3H, s), 3.99 (2H, t, J=7) 4.22 (2H, q, J=7), 5.05–5.12 (1H, m), 6.79 (1H, d, J=8), 6.95–7.31 (7H, m).

PREPARATIONS 16–30

The following compounds were prepared substantially according to the procedure in Preparation 15 substituting the indicated olefin for ethyl acrylate.

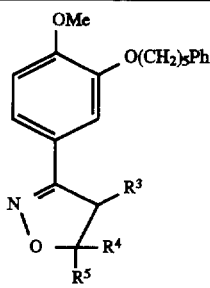

| Prep # | $R^5$ | $R^4$ | $R^3$ | Olefin | M.P. °C. | Data |
|---|---|---|---|---|---|---|
| 16 | $CO_2Et$ | Me | H | Ethyl α-methacrylate | oil | $^1$H NMR ($CDCl_3$): δ 1.25(3H, t, J=7), 1.37–1.90(6H, m), 1.64 (3H, s), 2.54(2H, t, J=7), 3.11(1H, d, J=15), 3.77(1H, d, J=15), 3.83(3H, s), 3.95(2H, q, J=7), 4.17(2H, q, J=7), 6.75(1H, d, J=8), 6.90–8.28(7H, m) |
| 17 | $CO_2Et$ | H | Me[a] | Ethyl crotonate | oil | MS(m/e): 425($M^+$), 279, 91(base) |
| 18 | $CO_2Et$ | Et | H | Cmpd of Prep 5 | oil | MS(m/e): 439($M^+$), 310, 105 |
| 19 | $CO_2Et$ | Pr | H | Cmpd of Prep 6 | oil | FABMS(m/e): 454($M^+$), 380, 310 |
| 20 | (S)—CONHCH—(Me)Ph[b] | H | H | Cmpd of Prep 9 | 85–90 | Anal. Calc'd for $C_{30}H_{34}N_2O_4$: C, 74.05; H, 7.04; N, 5.76. Found: C, 74.16; H, 6.93; N, 5.88. |
| 21 | (S)—CONHCH—(Me)Ph[c] | H | H | Cmpd of Prep 9 | 91–101 | Anal. Calc'd for $C_{30}H_{34}N_2O_4$: C, 74.05; H, 7.04; N, 5.76. Found: C, 74.32; H, 6.94; N, 5.71. |
| 22 | (S)—CONHCH—(Me)Ph[d] | Me | H | Cmpd of Prep 10 | 113–116 | Anal. Calc'd for $C_{31}H_{36}N_2O_4$: C, 74.37; H, 7.25; N, 5.60. Found: C, 74.17; H, 6.87; N, 5.53 |
| 23 | (R)—CONHCH—(Me)Ph[e] | Me | H | Cmpd of Prep 11 | 97–99 | Anal. Calc'd for $C_{31}H_{36}N_2O_4 \cdot \frac{1}{4} H_2O$: C, 73.64; H, 7.23; N, 5.55. Found: C, 73.83; H, 7.35; N, 5.60 |
| 24 | (R)—CONHCH—(Me)Ph[f] | Me | H | Cmpd of Prep 11 | 111–113 | Anal. Calc'd for $C_{31}H_{36}N_2O_4$: C, 74.37; H, 7.25; N, 5.60. Found: C, 74.51; H, 7.22; N, 5.43 |
| 25 | (R)—CONHCH—(Me)Ph[g] | Et | H | Cmpd of Prep 12 | 126–130 | $^1$H NMR ($CDCl_3$): δ 1.06(3H, t, J=7), 1.53(3H, d, J=7), 1.53–2.21 (8H, m), 2.65(2H, t, J=7); 3.23(1H, d, J=17), 3.67(1H, d, J=17), 3.89(3H, s), 4.02(2H, t, J=7), 5.02–5.15(1H, m), 6.85(1H, d, J=8), 7.02(1H, dd, J=2, 8), 7.16–7.32(12H, m) |
| 26 | (R)—CONHCH—(Me)Ph[g] | Et | H | Cmpd of Prep 12 | 121–123 | $^1$H NMR ($CDCl_3$): δ 0.92(3H, t, J=7), 1.47(3H, d, J=7), 1.47–2.18 (8H, m), 2.66(2H, t, J=7), 3.26(1H, d, J=17), 3.76(1H, d, J=17), 3.90(3H, s), 4.04(2H, t, J=7), 5.02–5.13(1H, m), 6.87(1H, d, J=8), 7.07(1H, dd, J=2, 8), 7.18–7.36(12H, m) |
| 27 | (R)—CONHCH—(Me)Ph[h] | Pr | H | Cmpd of Prep 13 | 123–125 | Anal. Calc'd for $C_{33}H_{40}N_2O_4 \cdot \frac{1}{4} H_2O$: C, 74.27, H, 7.60, N, 5.35. Found: C, 74.44; H, 7.50; N, 5.21 |
| 28 | (R)—CONHCH—(Me)Ph[i] | Pr | H | Cmpd of Prep 13 | 118–120 | Anal. Calc'd for $C_{33}H_{40}N_2O_4 \cdot \frac{1}{4} H_2O$: C, 74.27; H, 7.60; N, 5.25. Found: C, 74.08; H, 7.85; N, 5.19 |
| 29 | OAc | H | H | Vinyl acetate | oil | $^1$H NMR ($CDCl_3$): δ 1.46–1.95(6H, m), 2.17(3H, s), 2.62(2H, t, J=8), 3.30(1H, d, J=18), 3.54–3.60(1H, m), 3.87(3H, s), 4.02(2H, t, J=7), 5.27(1H, d, J=1), 6.82–7.30(8H, m) |
| 30 | $CO_2Me$ | $NHCO_2Bn$ | H | $H_2$=CH ($NHCO_2Bn$) $CO_2Me$ | oil | $^1$H NMR ($CDCl_3$): δ 1.35 –1.84(6H, m), 2.55(2H, t, J=7), 3.89 (3H, s), 3.93(2H, bd s), 3.94(2H, t, J=7), 4.01(3H, s), 5.01(2H, s), 6.30(1H, bd s), 6.73(1H, d, J=8), 6.90–7.33(12H, m) |

[a] trans stereochemistry
[b] less polar diastereomer - $R_f$ 0.23 (1:3 EtOAc-hexane)
[c] more polar diastereomer - $R_f$ 0.16 (1:3 EtOAc-hexane)
[d] more polar diastereomer - $R_f$ 0.42 (1:1 EtOAc-hexane)
[e] less polar diastereomer - $R_f$ 0.48 (1:1 EtOAc-hexane)
[f] more polar diastereomer - $R_f$ 0.42 (1:1 EtOAc-hexane)
[g] diastereomers of examples 25 and 26 were separated by fractional crystallization
[h] less polar diastereomer - $R_f$ 0.30 (3:7 EtOAc-hexane)
[i] more polar diastereomer - $R_f$ 0.26 (3:7 EtOAc-hexane)

PREPARATIONS 31–32

The following compounds were prepared substantially according to the procedure in Preparation 15 substituting the compound of Preparation 3 for the compound of Preparation 1 and substituting the indicated olefin for ethyl acrylate.

pound of Preparation 1. $^1$H NMR (CDCl$_3$): δ 1.31 (3H, t, J=7), 1.74–1.94 (4H, m), 2.68 (2H, t, J=7), 3.57–3.61 (2H, m), 3.87 (3H, s), 4.03 (2H, t, J=6), 4.25 (2H, q, J=7), 5.12 (1H, t, J=8), 6.83 (1H, d, J=8), 7.03 (1H, d, J=8), 7.16–7.35 (6H, m).

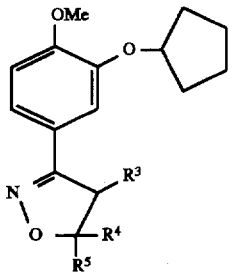

| Prep # | R$^5$ | R$^4$ | R$^3$ | Olefin | M.P. °C. | Data |
|---|---|---|---|---|---|---|
| 35 | CO$_2$Et | H | H | Ethyl acrylate | oil | $^1$H NMR (CDCl$_3$): δ 1.27(3H, t, J=7), 1.45–2.00(8H, m), 3.56(2H, d, J=10), 3.82(3H, s), 4.22(2H, q, J=7), 4.72–4.80(1H, m), 5.09(1H, t, J=10), 6.78(1H, d, J=8), 6.98(1H, d, J=8), 7.32(1H, s) |
| 32 | CO$_2$Et | Me | H | Ethyl methacrylate | 77–79 | $^1$H NMR (CDCl$_3$): δ 1.25(3H, t, J=7), 1.50–2.00(8H, m), 1.63(3H, s), 3.11(1H, d, J=17), 3.78(1H, d, J=17), 3.91(3H, s), 4.18(2H, q, J=7), 4.68–4.77(1H, m), 6.75(1H, d, J=8), 6.92(1H, dd, J=8, 2), 7.27(1H, d, J=2) |

PREPARATIONS 33–34

The following compounds were prepared substantially according to the procedure of Preparation 15 substituting the compound of Preparation 4 for the compound of Preparation 1 and substituting the indicated olefin for ethyl acrylate.

PREPARATION 36

Dimethyl Propenyl-2-phosphonate

The title compound was prepared as described by the method of Benezra, et al. (Benezra, C.; Nseic, S.; Qurisson, G. *Bull. Chem. Soc. Chim. Fr.*, 1967, 1140.)

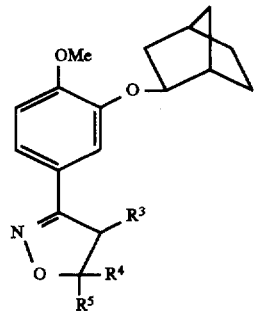

| Prep # | R$^5$ | R$^4$ | R$^3$ | Olefin | M.P. °C. | Data |
|---|---|---|---|---|---|---|
| 33 | CO$_2$Et | H | H | Ethyl acrylate | oil | $^1$H NMR (CDCl$_3$): δ 1.05–1.77(8H, m), 1.27(3H, t, J=7), 2.05(1H, bd s), 2.43(1H, bd s), 3.55(2H, d, J=10), 3.92(3H, s), 4.15–4.23(1H, m), 4.21(2H, q, J=7), 5.05(1H, t, J=10), 6.77(1H, d, J=8), 6.95(1H, d, J=8), 7.25(1H, s) |
| 34 | (R)—CHNHCH—(Me)Ph | Me | H | Cmpd of Prep 11* | 151–153 | $^1$H NMR (CDCl$_3$): δ 1.10–1.75(8H, m), 1.44(3H, d, J=7), 1.65(3H, s), 2.30(1H, bd s), 2.50(1H, bd d, J=4), 3.18(1H, d, J=17), 3.81(1H, d, J=17), 3.85(3H, s), 4.21(1H, d, J=7), 4.99–5.08(1H, m), 6.83(1H, d, J=8), 7.02(1H, dd, J=8, 2), 7.12(1H, d, J=9), 7.20–7.36(6H, m) |

*less polar diastereomer - R$_f$ 0.4 (3:7 EtOAc-hexane)

PREPARATION 35

3-[4-Methoxy-3-(5-phenylbutyloxy)]phenyl-2-isoxazoline-5-carboxylic Acid Ethyl Ester The compound of this Preparation was prepared as an oil, substantially according to the procedure of Preparation 15, substituting the compound of Preparation 2 for the com- Into a flask fitted with a reflux condenser was placed a mixture of 37 ml (29 g, 0.50 mol) of acetone and 46 ml (55 g, 0.50 ml) of dimethylphosphite followed by 3 ml of saturated methanolic sodium methoxide solution. A vigorous exotherm ensued and the mixture was allowed to stir at RT for about 16 h. A large deposit of crystals formed and were filtered and washed well with ether-hexane (1:1) to give 50 g of dimethyl 1-hydroxy-1-methylethylphosphonate, mp 75°–77° C.

A solution of 6.00 g (35.7 mmol) of dimethyl 1-hydroxy-1-methylethyl-phosphonate in 25 ml of pyridine was treated dropwise with 8.56 g (5.25 ml, 72.0 mmol) of thionyl chloride. The mixture was allowed to stir for about 16 h at RT and the solvent was removed by evaporation. The residue was diluted with 200 ml of water and extracted with EtOAc (3×200 ml). The combined extracts were dried ($Na_2SO_4$) and evaporated to 4.12 g of a yellow oil which was purified by flash chromatography (100 g of silica gel) using EtOAc as eluant to yield 3.46 g of the title compound as an oil.

PREPARATION 37

Diethyl 2-Methyl-1-propenyl-3-phosphonate

A mixture of 5.0 g (0.037 mol) of methallyl bromide and 15 g (0.087 mol) of triethyl phosphite was heated to about 160° C. for about 5 h. Purification of the crude reaction mixture by flash chromatography (300 g of silica gel) using an EtOAc-hexane (3:2) eluant afforded 3.6 g (50%) of the title compound as a light yellow oil. $^1$H NMR ($CDCl_3$): d 1.31 (6H, t, J=7), 1.87 (3H, d, J=3), 2.56 (2H, d, J=20), 4.03–4.13 (4H, m), 4.82–4.92 (2H, m).

PREPARATION 38

Diethyl 3-[4-Methoxy-3-(5-phenylpentyloxy)]phenyl-2-isoxazolin-5-ylphosphonate To a mixture of 1.02 g (7.76 mmol) of N-chlorosuccinimide, 0.05 ml of pyridine, and 30 ml of $CH_3Cl_2$ was added 2.00 g (6.38 mmol) of the compound Preparation 1 in 10 ml of $CH_2Cl_2$. The mixture was stirred for about 45 min at RT and 1.05 g (0.980 ml, 6.38 mmol) of diethyl vinylphosphonate was added followed by 0.777 g (1.07 ml, 7.66 mmol) of triethylamine. An exotherm ensued and the mixture became dark yellow. After stirring for about 2 h at RT, the mixture was diluted to 150 ml with $CH_2Cl_2$ and was washed with aqueous 1N HCl solution (2×100 ml), sat'd. aqueous $NaHCO_3$ solution (2×100 ml), dried ($MgSO_4$), and evaporated to 3.75 g of a yellow oil. Purification by flash chromatography (150 g of silica gel) using successively EtOAc-hexane (1:3), EtOAc, and MeOH—$CHCl_3$ (1:9) as eluants afforded 1.09 g of the title compound as an oil. $^1$H NMR ($CDCl_3$): d 1.30 (3H, t, J=7), 1.34 (3H, t, J=7), 1.40–1.90 (6H, m), 2.60 (2H, t, J=7), 3.52–3.65 (2H, m), 3.95 (3H, s), 3.99 (2H, t, J=7), 4.16–4.25 (4 H, m), 4.80 (1H, t, J=12), 6.80 (1H, d, J=8), 6.98–7.29 (7H, m).

PREPARATION 39–42

Reaction of the indicated oxime and olefin, analogous to the procedure of Preparation 38, afforded compounds having the following general structure:

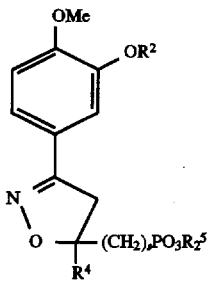

39. $R^2$ is $(CH_2)_5Ph$; $R^4$ is methyl; $R^5$ is methyl; s is 0; the oxime is the compound of Preparation 1; the olefin is the compound of Preparation 36; M.P. 91°–93° C.; $^1$H NMR ($CDCl_3$): d 1.46–1.92 (6H, m), 1.64 (3H, d, J=15), 2.62 (2H, t, J=7), 3.18 (1H, dd, J=17 and 19), 3.75–3.88 (10H, m), 4.00 (2H, t, J=7), 6.83 (1H, d, J=8), 7.00 (1H, d, J=8, 2), 7.14–7.33 (6H, m).

40. $R^2$ is $(CH_2)_5Ph$; $R^4$ is H; $R^5$ is ethyl; s is 1; the oxime is the compound of Preparation 1; the olefin is diethyl allylphosphonate; $^1$H NMR ($CDCl_3$): d 1.32 (3H, t, J=7), 1.34 (3H, t, J=7), 1.37–2.38 (8H, m), 2.61 (2H, t, J=7), 3.22–3.52 (2H, m), 3.86(3H, s), 4.00 (2H, t, J=7), 4.06–4.18 (4H, m), 4.82–4.96 (1H, m), 6.82 (1H, d, J=8), 7.03 (1H, dd, J=2, 8), 7.13–7.33 (6H, m).

41. $R^2$ is $(CH_2)_5Ph$; $R^4$ is methyl; $R^5$ ethyl; s is 1; the oxime is the compound of Preparation 1; the olefin is the compound of Preparation 37; $^1$H NMR ($CDCl_3$): d 1.30 (3H, t, J=7), 1.32 (3H, t, J=7), 1.28–1.90 (6H, m), 2.30 (2H, d, J=19), 2.61 (2H, t, J=7), 3.08 (1H, d, J=17), 3.63 (1H, d, J=17), 3.86 (3H, s), 4.00 (2H, t, J=7 ), 4.00–4.18 (4H, m), 6.82 (1H, d, J=8), 6.99 (1H, dd, J=2, 8), 7.11–7.32 (6H, m).

42. $R^2$ is cyclopentyl; $R^4$ is H; $R^5$ is ethyl, s is 0, the oxime is the compound of Preparation 3; the olefin is diethyl vinylphosphonate; $^1$H NMR ($CDCl_3$): d 1.31 (3H, t, J=7), 1.35 (3H, t, J=7), 1.50–2.00 (8H, m), 3.56–3.67 (2H, m), 3.85 (3 H, s), 4.17–4.25 (4H, m), 4.78–4.82 (2H, m), 6.83 (1H, d, J=8), 7.02 (1H, dd, J=2, 8), 7.32 (1H, d, J=2).

What is claimed is:
1. A compound of the formula

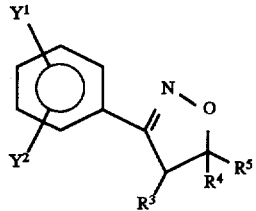

the racemic, racemic-diastereomeric mixtures and optical isomers of said compound and the pharmaceutically acceptable salts thereof wherein $Y^1$ is —$OR^1$ and is attached to the 4-position of the phenyl ring and $Y^2$ is —$OR^2$ and is attached to the 3-position of the phenyl ring;

$R^1$ is alkyl having 1 to 3 carbons, fluoromethyl, difluoromethyl or trifluoromethyl;

$R^2$ is ($C_3$–$C_7$)cycloalkyl, optionally substituted phenylalkyl having 1 to 6 carbons in the alkyl portion or bicycloalkyl having 6 to 9 carbons;

wherein the aromatic portion of the optionally substituted phenylalkyl is optionally independently substituted with ($C_1$–$C_4$) alkyl, ($C_1$–$C_4$) alkoxy, halogen or $CF_3$;

$R^3$ is hydrogen, $(C_1-C_3)$alkyl, mono-hydroxyalkyl having 1 to 3 carbons or alkoxyalkyl having 1 to 3 carbons in the alkyl portion and 1 to 3 carbons in the alkoxy portion;

$R^4$ is hydrogen, $(C_1-C_5)$alkyl, —COOH, alkoxyalkyl having 1 to 3 carbons in the alkyl portion and 1 to 3 carbons in the alkoxy portion, N-alkylaminoalkyl having 1 to 3 carbons in the alkylamino portion and 1 to 3 carbons in the alkyl portion or N,N-dialkylaminoalkyl having a total of 2 to 6 carbons in the dialkylamino portion and 1 to 3 carbons in the alkyl portion;

or $R^3$ and $R^4$ are taken together with the carbon atoms to which they are attached and form —CH$_2$OCH$_2$OCH$_2$—; and $R^5$ is hydrogen, —CHO, amino, aminoalkyl having 1 to 3 carbons,

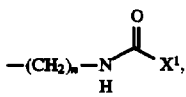

mono-hydroxyalkyl having 1 to 3 carbons, —(CH$_2$)$_b$—COOR$^6$, —COR$^7$, —(CH$_2$)$_m$CO$_2$H, $(C_1-C_4)$ alkyl, hydroxy, —(CH$_2$)$_q$CONX$^2$X$^3$, —(CH$_2$)$_r$SO$_2$NX$^4$X$^5$, —(CH$_2$)$_t$PO$_3$H$_2$ or

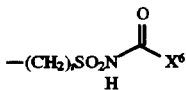

wherein b is 0 or an integer from 1 to 6;
m, n, q, r, s and t are independently 0, 1, 2, 3 or 4;
$R^6$ and $R^7$ are each independently $(C_1-C_4)$alkyl;
$X^1$ is hydrogen, $(C_1-C_4)$ alkyl, —O$(C_1-C_4)$ alkyl or alkoxyphenyl having one to four carbon atoms in the alkoxy portion;
$X^2$, $X^3$, $X^4$ and $X^5$ are each independently hydrogen or $(C_1-C_3)$ alkyl; and
$X^6$ is $(C_1-C_3)$alkyl or phenyl;
provided that when $R^4$ is —COOH then $R^5$ is not —COOH.

2. A compound according to claim 1 wherein $R^1$ is methyl; $R^2$ is $(C_3-C_7)$cycloalkyl, bicycloalkyl having 6 to 9 carbons, or phenylalkyl having 1 to 6 carbons in the alkyl portion; $R^3$ is hydrogen or $(C_1-C_3)$alkyl; $R^4$ is hydrogen or $(C_1-C_5)$alkyl and $R^5$ is —(CH$_2$)$_m$CO$_2$H, —CHO, —COCH$_3$, amino, hydroxy, mono-hydroxyalkyl having 1 to 3 carbons, aminoalkyl having 1 to 3 carbons, or

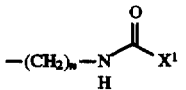

wherein $X^1$ is $(C_1-C_4)$alkyl or alkoxyphenyl having one to four carbon atoms in the alkoxy portion and n is 0 or an integer from 1 to 3.

3. A compound according to claim 2 wherein $R^2$ is cyclopentyl or phenylalkyl having 4 or 5 carbons in the alkyl portion.

4. A compound according to claim 3 wherein $R^2$ is 5-phenylpentyl.

5. A compound according to claim 4 wherein $R^5$ is —(CH$_2$)$_m$CO$_2$H, —CHO, —COCH$_3$, hydroxy or mono-hydroxyalkyl having 1 to 3 carbons.

6. A compound according to claim 5 wherein $R^5$ is —(CH$_2$)$_m$CO$_2$H.

7. A compound according to claim 6 wherein $R^5$ is hydrogen; $R^4$ is hydrogen or $(C_1-C_5)$alkyl and m=0.

8. A compound according to claim 7 wherein $R^4$ is hydrogen, methyl, ethyl or propyl.

9. A compound according to claim 8 wherein the compound is (+) or (−)-5-ethyl-3-[4-methoxy-3-(5-phenylpentyloxy)]-phenyl-2-isoxazoline-5-carboxylic acid.

10. A compound according to claim 9 wherein the compound is (−)-5-ethyl-3-[4-methoxy-3-(5-phenylpentyloxy)]phenyl-2-isoxazoline-5-carboxylic acid.

11. A compound according to claim 1 wherein R is CH$_3$; R is 5-phenyl-pentyl; $R^3$ is hydrogen; $R^4$ is hydrogen or CH$_3$ and $R^5$ is —(CH$_2$)$_s$PO$_3$H$_2$ wherein s is 0 or 1.

12. A compound according to claim 1 wherein $R^1$ is CH$_3$; $R^2$ is cyclopentyl; $R^3$ is hydrogen; $R^4$ is hydrogen and $R^5$ is —(CH$_2$)$_s$PO$_3$H$_2$ wherein s is 0.

13. A pharmaceutical composition comprising an effective amount of a compound according to claim 1 and a pharmaceutically acceptable diluent or carrier.

14. A method of inhibiting phosphodiesterase type IV in a mammal in need thereof which comprises administering to said mammal a phosphodiesterase IV inhibiting amount of a compound according to claim 1.

15. A method of treating an inflammatory condition in a mammal in need thereof which comprises administering to said mammal an antiinflammatory amount of a compound according to claim 1.

16. A method of treating AIDS, asthma, arthritis, bronchitis, chronic obstructive pulmonary disease, psoriasis, allergic rhinitis, dermatitis or shock in a mammal in need thereof which comprises administering to said mammal an effective amount of a compound according to claim 1.

* * * * *

UNITED STATES PATENT AND TRADEMARK OFFICE
CERTIFICATE OF CORRECTION

PATENT NO. : 5,686,434
DATED : November 11, 1997
INVENTOR(S) : Edward Fox Kleinman It is certified that error appears in the above-identified patent and that said Letters Patent is hereby corrected as shown below:

Column 6, line 25 "(i.e., -CO(OH)alkyl)" should read -- (i.e., -CH(OH)alkyl) --
Column 22, line 37 "d, J=6)" should read -- d, J=8) --
Column 24, Example 43, "$(CH_2)_4Ph$" should read -- $(CH_2)_5Ph$ --
Column 25, line 41, "(2H, t, d=7)" should read -- (2H, t, J=7) --
Column 28, line 12, "BOAc" should read -- EtOAc --
Column 30, Preparation 27, "N, 535." should read -- N, : 5.25--.
Column 29, Preparation 30, "$H_2$=CH" should read -- $H_2C$=CH --
Column 31, Preparation 35, "35" should read --31 --
Column 33, line 43, "$CH_3Cl_2$" should read -- $CH_2Cl_2$ --
Column 36, line 15, "wherein $R^5$ is" should read -- wherein $R^3$ is --
Column 36, line 29, "wherein R is $CH_3$" should read -- wherein $R^1$ is $CH_3$ --; and
Column 36, line 30, "R is 5-phenyl-pentyl;" should read --$R^2$ is 5-phenyl-pentyl;--

Signed and Sealed this

Seventh Day of December, 1999

Attest:

*Attesting Officer*

Q. TODD DICKINSON

*Acting Commissioner of Patents and Trademarks*